(12) United States Patent
Romero-Ortega et al.

(10) Patent No.: US 11,311,720 B2
(45) Date of Patent: Apr. 26, 2022

(54) METHODS OF MAKING AND BIOELECTRONIC APPLICATIONS OF METALIZED GRAPHENE FIBERS

(71) Applicants: Board of Regents, The University of Texas System, Austin, TX (US); University of Wollongong, Wollongong (AU)

(72) Inventors: Mario Romero-Ortega, Coppell, TX (US); Gordon Wallace, Wollongong (AU); Maria Gonzalez Gonzalez, Dallas, TX (US); Rouhollah Ali Jalili, Melbourne (AU)

(73) Assignees: University of Wollongong, Wollongong (AU); Board of Regents, The University of Texas System, Austin, TX (US)

( * ) Notice: Subject to any disclaimer, the term of this patent is extended or adjusted under 35 U.S.C. 154(b) by 214 days.

(21) Appl. No.: 16/691,309

(22) Filed: Nov. 21, 2019

(65) Prior Publication Data
US 2020/0155834 A1 May 21, 2020

Related U.S. Application Data

(60) Provisional application No. 62/770,540, filed on Nov. 21, 2018.

(51) Int. Cl.
| | |
|---|---|
| *H01M 4/96* | (2006.01) |
| *C23C 14/34* | (2006.01) |
| *A61N 1/05* | (2006.01) |
| *C23C 14/18* | (2006.01) |

(52) U.S. Cl.
CPC .......... *A61N 1/0556* (2013.01); *C23C 14/185* (2013.01); *C23C 14/34* (2013.01); *H01M 4/96* (2013.01)

(58) Field of Classification Search
None
See application file for complete search history.

(56) References Cited

U.S. PATENT DOCUMENTS

2013/0090542 A1  4/2013  Kipke et al.

OTHER PUBLICATIONS

Kozai et al, "Chronic In Vivo Evaluation of PEDOT/CNT for Stable Neural Recordings", IEEE Transactions on Biomedical Engineering, vol. 63, No. 1, pp. 111-119, Jun. 15, 2015.
Bofretius et al, "On the Stability of Poly—Ethylenedioxythiopene as Coating Material for Active Neural Implants", Artificial Organs, vol. 35, No. 3, pp. 245-248, Mar. 15, 2011.

(Continued)

*Primary Examiner* — Tracy M Dove
(74) *Attorney, Agent, or Firm* — Nutter McClennen & Fish LLP

(57) ABSTRACT

The present disclosure provides methods of making and applying metallized graphene fibers in bioelectronics applications. For example, platinized graphene fibers may be used as an implantable conductive suture for neural and neuro-muscular interfaces in chronic applications. In some embodiments, an implantable electrode includes a multi-layer graphene-fiber core, an insulative coating surrounding the multi-layer graphene-fiber core, and a metal layer disposed between the multi-layer graphene-fiber core and the insulative coating.

20 Claims, 37 Drawing Sheets
(25 of 37 Drawing Sheet(s) Filed in Color)

(56) References Cited

OTHER PUBLICATIONS

Green et al, "Impact of co-incorporating laminin peptide dopants and neurotrophic growth factors on conducting polymer properties", Acta Biomaterialia, vol. 6, No. 1, pp. 63-71, Jan. 2010.
Green et al, "Conducting polymers for neural interfaces: Challenges in developing an effective long-term implant", Biomaterials, vol. 29, No. 24-25, pp. 3393-3399, Aug.-Sep. 2008.
Qi et al, "Design of Architectures and Materials in In—Plane Micro—supercapacitors: Current Status and Future Challenges", Advanced Materials, vol. 29, No. 5, p. 1602802, Feb. 2, 2017.
Cheng et al, "Functional Graphene Nanomaterials Based Architectures: Biointeractions, Fabrications, and Emerging Biological Applications", Chem. Rev. Vol. 117, vol. 3, pp. 1826-19914, Jan. 11, 2017.
Sahni et al, "Biocompatibility of pristine graphene for neuronal interface", Journal of Neurosurgery, vol. 11, No. 5, pp. 489-614, May 2013.
Cheng et al, "A Water-Processable and Bioactive Multivalent Graphene Nanoink for Highly Flexible Films and Nanofibers", Advanced Materials, (2017).
Harreither et al, "Carbon Nanotube Fiber Microelectrodes Show a Higher Resistance to Dopamine Fouling", Anal. Chem, vol. 85, No. 15, pp. 7447-7453, Jun. 22, 2013.
Wang et al, "Carbon Nanotube Fiber Microelectrodes", J. Am. Chem. Soc., vol. 125, No. 48, pp. 14706-14707, Nov. 8, 2003.
Yoon et al, "Intracellular Neural Recording with Pure Carbon Nanotube Probes", PLoS One, vol. 8, No. 6, pp. 65715, Jun. 19, 2013.
Zhang et al, "Tissue-Compliant Neural Implants from Microfabricated Carbon Nanotube Multilayer Composite", ACS Nano, vol. 7, No. 9, pp. 7619-7629, Aug. 9, 2013.
Jiang et al, "Superaligned Carbon Nanotube Arrays, Films, and Yarns: A Road to Applications", vol. 23, No. 9, pp. 1154-1161, Jan. 31, 2011.
Zhao et al, "Single wall carbon nanotube fibers extruded from super-acid suspensions: Preferred orientation electrical and thermal transport", Journal of Applied Physics, vol. 95, No. 2, pp. 649-655, Jan. 15, 2004.
Kou et al, "A Mini Review on Nanocarbon-Based 1D Macroscopic Fibers: Assembly Strategies and Mechanical Properties", Nano-Micro Letters, vol. 9, No. 51, (2017).
Schrimer et al, "Conductive composite fibres from reduced graphene oxide and polypyrrole nanoparticles", Journal of Materials Chemistry B, No. 6, (2016).
Esrafilzadeh et al, "High—Performance Multifunctional Graphene—PLGA Fibers: Toward Biomimetic and Conducting 3D Scaffolds", vol. 26, No. 18, pp. 3105-3117, May 10, 2016.
Rho et al, "Metal nanofibrils embedded in long free-standing carbon nanotube fibers with a high critical current density", NPG Asia Materials, vol. 10, pp. 146-155, (2018).
Poulin et al, "Superflexibility of graphene oxide", PNAS, vol. 113, No. 40, pp. 11088-11093, Oct. 4, 2016.
Jalili et al, "Formation and processability of liquid crystalline dispersions of graphene oxide", Materials Horizons, vol. 1, No. 87, pp. 87-91, Aug. 23, 2013.
Jalili et al, "Scalable One—Step Wet—Spinning of Graphene Fibers and Yarns from Liquid Crystalline Dispersions of Graphene Oxide: Towards Multifunctional Textiles", Advanced Functional Materials, vol. 23, No. 43, pp. 5345-5354, Nov. 20, 2013.
Potter et al, "Stab injury and device implantation within the brain results in inversely multiphasic neuroinflammatory and neurodegenerative responses", J. Neural Eng., vol. 9, (2012).
Kozai et al, "Chronic tissue response to carboxymethyl cellulose based dissolvable insertion needle for ultra-small neural", Biomaterials, vol. 35, No. 34, pp. 9255-9268, Nov. 2014.
Cortés-Salazar et al, "Parylene C coated microelectrodes for scanning electrochemical microscopy", Electrochimica Acta, vol. 110, No. 1, pp. 22-29, Nov. 2013.
Hassler et al, "Characterization of parylene C as an encapsulation material for implanted neural prostheses", Journal of Biomedical Materials Research, vol. 93B, No. 1, Jan. 29, 2010.
Fontes, "Electrodes for bio-application: recording and stimulation", Journal of Physics: Conference Series, vol. 421, Oct. 2012.
Barrese et al, "Scanning electron microscopy of chronically implanted intracortical microelectrode arrays in non-human primates", Journal of Neural Engineering, vol. 13, No. 2, Jan. 29, 2016.
Irwin et al, "Chronic recording of hand prosthesis control signals via a regenerative peripheral nerve interface in a rhesus macaque", Journal of Neural Engineering, vol. 13, No. 4, Jun. 1, 2016.
Kim et al, "Conducting polymers on hydrogel-coated neural electrode provide sensitive neural recordings in auditory cortex", Acta Biomaterialia, vol. 6, No. 1, pp. 57-62, Jan. 2010.
Guitchounts et al, "A carbon-fiber electrode array for long-term neural recording", Journal of Neural Engineering, vol. 10, No. 4, Jul. 17, 2013.
Kozai et al, "Ultrasmall implantable composite microelectrodes with bioactive surfaces for chronic neural interfaces", Nature Materials, vol. 11, pp. 10656-1073, Nov. 11, 2012.
Lu et al, "Electrodeposited polypyrrole/carbon nanotubes composite films electrodes for neural interfaces", Biomaterials, vol. 31, No. 19, pp. 5169-5181, Jul. 2010.
Boehler et al, "Nanostructured platinum grass enables superior impedance reduction for neural microelectrodes", Biomaterials, vol. 67, pp. 346-353, Oct. 2015.
Wilks et al, "Poly(3,4-ethylenedioxythiophene) as a micro-neural interface material for electrostimulation", Front. Neuroeng., Jun. 9, 2009.
Wang et al, "Neural Stimulation with a Carbon Nanotube Microelectrode Array", Nano Lett., vol. 6, No. 9, pp. 2043-2048, Aug. 26, 2006.
Lu et al, "Flexible Neural Electrode Array Based-on Porous Graphene for Cortical Microstimulation and Sensing", Scientific Reports, vol. 6, pp. 33526 Sep. 19, 2016.
Liu et al, "Implantable Graphene-based Neural Electrode Interfaces for Electrophysiology and Neurochemistry in In Vivo Hyperactue Stroke Model", ACS Appl. Mater. Interfaces, vol. 8, No. 1, pp. 187-196, Dec. 14, 2015.
Zheng et al, "Hierarchically porous sheath-core graphene-based fiber-shaped supercapacitors with high energy density", Journal of Materials Chemistry A, vol. 6, No. 3, pp. 896-907, Nov. 6, 2017.
Wang et al, "High-Performance Graphene-Fiber-Based Neural Recording Microelectrodes", Advanced Materials, vol. 31, No. 15, Apr. 12, 2019.
PCT International Application No. PCT/US19/62663, International Search Report of the International Searching Authority, dated Feb. 12, 2020, 3 pages.
PCT International Application No. PCT/US19/62663, Written Opinion of the International Searching Authority, dated Feb. 12, 2020, 8 pages.
Loeb et al, "Cuff electrodes for chronic stimulation and recording of peripheral nerve activity", J Neurosci Methods, vol. 64, No. 1, pp. 95-103, (1996).
Tan et al, "Stability and selectivity of a chronic, multi-contact cuff electrode for sensory stimulation in human amputees", J Neural Eng, vol. 12, No. 2, p. 026002, (2015).
Kim et al, "Material considerations for peripheral nerve interfacing", MRS Bulletin, vol. 37, No. 6, pp. 573-580, (2012).
Cogan et al, "In vitro comparison of the charge-infection limits of activated iridium oxide (AIROF) and platinum-iridium microelectrodes", IEEE Transactions on Biomedical Engineering, vol. 52, No. 9, pp. 1612-1614, (2005).
Brummer et al, "Criteria for selecting electrodes for electrical stimulation: theoretical and practical considerations", Annals of the New York Academy of Sciences, vol. 405. No. 1, pp. 159-171, (1983).
Cogan et al, "Over-pulsing degrades activated iridium oxide films used for intracortical neural stimulation", Journal of Neuroscience Methods, vol. 137, No. 2, pp. 141-150, (2004).
Negi et al, "Neural electrode degradation from continuous electrical stimulation: Comparison of sputtered and activated iridium oxide", Journal of Neuroscience Methods, vol. 186, No. 1, pp. 8-17, (2010).

(56) References Cited

OTHER PUBLICATIONS

Keefer et al, "Carbon nanotube coating improves neuronal recordings", Nat Nanotechnol, vol. 3, No. 7, pp. 434-439, (2008).
Luo et al, "Highly stable carbon nanotube doped poly(3,4-ethylenedioxythiophene) for chronic neural stimulation", Biomaterials, vol. 32, No. 4, pp. 5551-5557, (2011).
Vitale et al, "Neural stimulation and recording with bidirectional, soft carbon nanotube fiber microelectrodes", ACS Nano, vol. 9, No. 4, pp. 4465-4474, (2015).
McCallum et al, "Chronic interfacing with the autonomic nervous system using carbon nanotube (CNT) yarn electrodes", Sci Rep, vol. 7, No. 1, pp. 11723, (2017).
Li et al, "Processable aqueous dispersions of graphene nanosheets", Nat Nantechnol, vol. 3, No. 2, pp. 101-105, (2008).
Aboutalebi et al, "High-performance multifunctional graphene yarns: toward wearable all-carbon energy storage textiles", ACS Nano, vol. 8, No. 3, pp. 2456-2466, (2014).
Tjoa et al, "Facile photochemical synthesis of graphene-pt nanoparticle composite for counter electrode in dye sensitized solar cells", ACS Appl Mater Interfaces, vol. 4, No. 7, pp. 3447-3452, (2012).
Navarro et al, "A critical review of interfaces with the peripheral nervous system for the control of neuroprostheses and hybrid bionic systems", J Peripher Nerv Syst, vol. 10, No. 3, pp. 229-258, (2005).
Naples et al, "A spiral nerve cuff electrode for peripheral nerve stimulation", IEEE Trans Biomed Eng, vol. 35, No. 11, pp. 905-916, (1988).
Rutten et al, "Selective electrical interfaces with the nervous system", Annu Rev Biomed Eng, vol. 4, pp. 407-452, (2002).
Stein et al, "Principles underlying new methods for chronic neural recording", Can J Neurol Sci, vol. 2, No. 3, pp. 235-244, (1975).
Christie et al, "Long-term stability of stimulating spinal nerve cuff electrodes on human peripheral nerves", J Neuroeng Rehabil, vol. 14, No. 1, pp. 70, (2017).
Ordonez et al, "Cuff electrodes for very small diameter nerves—prototyping and first recordings in vivo", Conf Proc IEEE Eng Med Biol Soc, vol. 2014, pp. 6846-6849, (2014).
Lacour et al, "Flexible and stretchable micro-electrodes for in vitro an in vivo neural interfaces", Med Biol Eng Comput, vol. 48, No. 10, pp. 945-954, (2010).
Restaino et al, "Biomechanical and functional variation in rat sciatic nerve following cuff electrode implantation", J Neuroeng Rehabil, vol. 11, pp. 73, (2014).
Vince et al, "Anti-TNF-alpha reduces the inflammatory reaction associated with cuff electrode implantation around the sciatic nerve", J Neuroimmunol, vol. 165, No. 1-2, pp. 121-128, (2005).
Wodlinger et al, "Recovery of neural activity from nerve cuff electrodes", Conf Proc IEEE Eng Med Biol Soc, vol. 2011, pp. 4653-4656, (2011).
Christensen et al, "The foreign body response and morphometric changes associated with mesh-style peripheral nerve cuffs", Acta Biomater, vol. 67, pp. 79-86, (2018).
Birmingham et al, "Bioelectronic medicines: a research roadmap", Nat Rev Drug Discov, vol. 13, No. 6, pp. 399-400, (2014).
McDonald, "Morphology of the rat carotid sinus nerve. II. Number and size of axons", J Neurocytol, vol. 12, No. 3, pp. 373-392, (1983).
Sevcencu et al, "A neural blood pressure marker for bioelectronic medicines for treatment of hypertension", Biosens Bioelectron, vol. 98, pp. 1-6, (2017).

Kim et al, "Electrochemical detection of dopamine in the presence of ascorbic acid using graphene modified electrodes", Biosens Bioelectron, vol. 25, No. 10, pp. 2366-2369, (2010).
Gunasekea et al, "Intracortical Recording Interfaces: Current Challenges to Chronic Recording Function", ACS Chem Neurosci, vol. 6, No. 1, pp. 68-83, Jan. 14, 2015.
Vitale et al, "Fluidic Microactuation of Flexible Electrodes for Neural Recording", Nano Lett, vol. 18, No. 1, pp. 326-335, Dec. 8, 2017.
Rivnay et al, "Next-generation probes, particles, and proteins for neural interfacing", Science Advances, vol. 3, No. 6, pp. e1601649, Jun. 9, 2017.
Won et al, "Recent Advances in Materials, Devices, and Systems for Neural Interfaces", Advanced Materials, vol. 30, No. 30, pp. 1800534, Jul. 26, 2018.
Wang et al, "Nanotechnology and Nanomaterials for Improving Neural Interfaces", Advanced Functional Materials, vol. 28, Jul. 2017.
Tybrandt et al, "High-Density Stretchable Electrode Grids for Chronic Neural Recording", Advanced Materials, vol. 30, (2018).
Cogan, "Neural Stimulation and Recording Electrodes", Annual Review of Biomedical Engineering, vol. 10, pp. 275-309, Aug. 15, 2008.
Lissandrello et al, "A micro-scale printable nanoclip for electrical stimulation and recording in small nerves", Journal of Neural Engineering, vol. 14, Mar. 21, 2017.
Lee et al, "Strategies for Minimizing Glial Response to Chronically-implanted Microelectrode Arrays for Neural Interface", Biomed Eng Lett, vol. 4, pp. 120-128, Jun. 10, 2014.
Ganji et al, "Development and Translation of PEDOT: PSS Microelectrodes for Intraoperative Monitoring", Advanced Functional Materials, (2017).
Zhao et al, "Programmable Hydrogel Ionic Circuits for Biologically Matched Electronic Interfaces" Advanced Materials, vol. 30, (2018).
Tong et al, "Optimizing growth and post treatment of diamond for high capacitance neural interfaces", Biomaterials, vol. 104, pp. 32-42, Oct. 2016.
Harris et al, "Measuring the effective area and charge density of platinum electrodes for bionic devices", vol. 15, (2018).
Garrett et al, "Ultra-nanocrystalline diamond electrodes: Optimization towards neural stimulation applications", J. Neural Eng., vol. 9, Dec. 7, 2011.
Weremfo et al, "Investigating the Interfacial Properties of Electrochemically Roughened Platinum Electrodes for Neural Stimulation", Langmuir, vol. 31, No. 8, pp. 2593-2599, Feb. 10, 2015.
Cogan et al, "Tissue damage thresholds during therapeutic electrical stimulation", J. Neural Eng., vol. 13, Jan. 20, 2016.
Weiland et al, "In vitro electrical properties for iridium oxide versus titanium nitride stimulating electrodes", IEEE Trans. Biomed. Eng., vol. 49, No. 12, pp. 1574-1579, Dec. 2002.
Charkhkar et al, "Chronic intracortical neural recordings using microelectrode arrays coated with PEDOT-TFB", Acta Biomaterialia, vol. 32, No. 1, pp. 57-67, Mar. 2016.
Venkatraman, "In Vitro and In Vivo Evaluation for Neural Stimulation for Neural Stimulation and Recording", IEEE Transactions on Neural Systems and Rehabilitation Engineering, vol. 19, No. 3, Jun. 2011.
Green et al, "Substrate dependent stability of conducting polymer coatings on medical electrodes", Biomaterials, vol. 33, No. 25, pp. 5875-5886, Sep. 2012.
Gerwig et al, "PEDOT-CNT composite microelectrodes for recording and electrostimulation applications: fabrication, morphology, and electrical properties", Front. Neuroeng., May 4, 2012.

METHODS OF MAKING AND BIOELECTRONIC APPLICATIONS OF METALIZED GRAPHENE FIBERS

CROSS REFERENCE TO RELATED APPLICATIONS

This application claims priority to and the benefit of U.S. Provisional Application No. 62/770,540 entitled "Methods of Making and Bioelectronic Applications of Metallized Graphene Fibers" filed on Nov. 21, 2018, the contents of which is hereby incorporated by reference in its entirety.

TECHNICAL FIELD

The present disclosure is related to the making biosensors and bioelectronics applications of microelectrode arrays including metallized graphene fibers.

BACKGROUND

Chronically implantable microelectrodes enable communication between man-made devices and the nervous system. Neural prostheses and therapies based on electrical stimulation or action potential recording, involve electrodes interfaced to central and peripheral nervous systems. A functional microelectrode is required to communicate with an individual neuron to record bio-signals, while delivering sufficient amount of electrical charge to depolarize the neural tissue and initiate a response. Existing microelectrode technologies have met significant challenges and limitations.

For example, while effective bidirectional communication between a machine and the nervous system requires access to a low impedance soft microelectrode with a tip size comparable to individual neurons (D<50 µm and geometric surface area<2000 $\mu m^2$), the performance of conventional microelectrodes comprised of noble metals (i.e., gold, platinum (Pt) and platinum/iridium) and crystalline silicon is limited due to their high impedance, low charge injection capacity (0.05-0.26 $mC/cm^2$), low surface area and mechanical mismatch between the electrode and surrounding tissue causing scarring and failure of the device.

Accordingly, the selection of material for electrodes at the interfaces for neural stimulation and recording influences the efficacy, reliability and lifetime of neural interfaces. Furthermore, during the stimulation and recording, the electrode must deliver and record sufficient amount of charge, but not exceed the threshold for triggering electrolysis of the surrounding media. The low surface area of conventional metal-based electrodes intrinsically limits their ability to deliver a high charge density and adversely affects the sensitivity of individual neuron signal recording.

These limitations have motivated the evaluation of other materials such as nano structured carbon, nanostructured fibers, metal oxides, metal nitrides and organic conductors, to provide enhanced electrochemical characteristics with biocompatibility. However, such materials provide additional challenges. For example, coating with titanium nitride (TiN) improves the charge injection capacity of Pt electrodes from 0.05-0.26 $mC/cm^2$ to 0.87 $mC/cm^2$ over a capacitive mechanism, which is favorable for in-vivo studies. Activated Iridium oxide (IrOx) further enhances the charge injection capacity of Pt electrodes to 1-5 $mC/cm^2$ through a faradaic mechanism, however, it has limited stability and safety margin for neural stimulation. Deposition of conducting polymers such as PEDOT:PSS, PEDOT:pTS, PEDOT:$ClO_4$, PEDOT:CNT further increase the charge injection capacity to 2.92, 2.01, 2.09, and 1.25 $mC/cm^2$, respectively, compared with Pt (0.05-0.26 $mC/cm^2$). These polymers also reduce the electrode impedance to 8, 26.5, 203 and 42 $M\Omega$ $\mu m^2$, respectively, compared with Pt (~390 $M\Omega$ µm). However, the heterogeneous nature of the coated microelectrode is prone to galvanic coupling that can result in side reactions, corrosion, delamination and consequently early failure. The selected materials and fabrication process must also minimize electrode delamination to ensure robust and reliable operation.

In addition, conventional low impedance microelectrodes are not stiff enough to penetrate the soft nerve tissue, yet flexible or stretchable to minimize mechanical mismatch with the tissue and accommodate for micromovements once implanted.

Nanostructured carbonaceous materials including graphene can provide outstanding electrochemical characteristics while enabling flexibility and strength. Nanotubes and graphene microfibers provide excellent electrochemical properties, high surface area, mechanical strength, high flexibility, and biocompatibility, and thus ideal for electrode fabrication. Indeed, carbon nanotube fibers demonstrated significant electrochemical activity, sensitivity, and resistance to biofouling when implanted, compared with metal electrodes and conventional carbon fibers. However, while the neat carbon nanotube based fiber microelectrodes are stable and able to record neural activity for relatively long periods of time, the spinning process used to manufacture nanotubes is challenging. Additionally, the high cost for producing super aligned carbon nanotube arrays (dry spinning), as well as the extremely rigorous conditions needed for their manufacturing including high temperature (>1000° C.), and the use of corrosive solvents (e.g. fuming sulfuric acid and chlorosulphonic acid), drastically limits the production of carbon nanotube-based microfibers.

Furthermore, an additional major drawback of conventional free-standing carbon nanotubes and graphene microfibers lies in the high resistivity compared with their metallic counterparts. When a microelectrode is longer than a few millimeters, the resistivity increases significantly, which poses a significant challenge to low noise recording.

SUMMARY

The present disclosure is related to the making biosensors and bioelectronics applications of microelectrode arrays including metallized graphene fibers. In some embodiments, the fabrication of flexible and free-standing graphene-fiber based microelectrode arrays with a thin platinum coating, as a current collector, results in a structure with low impedance, high surface area and excellent electrochemical properties. The graphene-fibers may be manufactured using liquid crystalline dispersions of graphene oxide (LCGO). The graphene fibers have unique mechanical and electrochemical properties in addition to its natural biocompatibility. The resulting microelectrode arrays provide better performance when compared to conventional graphene or Pt electrodes. In particular, in some embodiments, the low impedance and porous structure of graphene fiber results in an unrivaled charge injection capacity and the improved ability to record and detect neuronal activity, while the thin Pt layer transfers the collected electrons along the microelectrode efficiently. Further, the resulting microelectrode arrays can also detect neuronal activity with improved signal to noise ratios when compared to conventional microelectrode arrays.

In some embodiments, an implantable electrode includes a multi-layer graphene-fiber core, an insulative coating surrounding the multi-layer graphene-fiber core, and a metal layer disposed between the multi-layer graphene-fiber core and the insulative coating. In some embodiments, the multi-layer graphene-fiber core does not include a binder material. Optionally, the insulative coating may be polymer-based coating such as Parylene-C or silicone. In some embodiments, the insulative coating has a thickness of about 2 μm. In some embodiments the metal layer may be adjacent to the multi-layer graphene-fiber core and the metal layer covers completely or a surface portion of the graphene-fiber core with total or partial encapsulation of the multi-layer graphene-fiber core. In some embodiments, the metal layer covers about half of the surface of the multi-layer graphene-fiber core. In some embodiments, the metal layer is adjacent the multi-layer graphene-fiber core and the metal layer covers a surface portion of the graphene-fiber core with complete encapsulation of the multi-layer graphene-fiber core. In some embodiments, the metal layer comprises at least one of platinum, iridium, iridium oxide, platinum-iridium, and titanium nitride. In some embodiments, the metal layer has thickness in the range between about 10 nm to about 500 nm. In some embodiments, the multi-layer graphene-fiber core has a diameter in the range of between about 10 μm to about 200 μm.

In some embodiments, a method for making an implantable electrode includes the steps of forming a multi-layered graphene-fiber core by performing an in-situ reduction of fully ordered graphene oxide sheets in a liquid crystalline, coating at least a portion of the multi-layered graphene-fiber core with a metal layer, and coating the multi-layered graphene-fiber core and metal layer with an insulative coating. Forming a multi-layered graphene-fiber core by performing an in-situ reduction may include the step of wet-spinning liquid crystalline dispersions of graphene oxide using a coagulation bath containing an acid. Optionally, the acid includes hyporphosphorous acid. Optionally, the metal layer includes at least one of platinum, iridium, iridium oxide, platinum-iridium, and titanium nitride. Optionally, the metal layer has thickness in the range between about 10 nm to about 500 nm. Optionally the insulative coating includes Parylene-C.

In some embodiments, a method of recording and stimulating a peripheral includes implanting an implantable electrode by engaging the peripheral nerve, where the implantable electrode further comprises a multi-layer graphene-fiber core, an insulative coating surrounding the multi-layer graphene fiber core, and a metal layer disposed between the multi-layer graphene-fiber core and the insulative coating, and at least one of recording and stimulating from the peripheral nerve. Optionally, engaging a peripheral nerve may include implanting the implantable electrode inside the peripheral nerve, sutured through the peripheral nerve, or over the peripheral nerve. Optionally, the peripheral nerve may innervate one or more organs including heart, lungs, stomach, liver, pancreas, kidney and those in the pelvic and perineal areas, among others. In some embodiments, a system may be used to record and/or stimulate from autonomic or sematosensory ganglia, including, but not limited to, the nodose, mesentheric and carotid. Additionally, in some embodiments, systems and methods built in accordance with the present disclosure may be used to record from and/or stimulate neurovascular plexi, where nerve branches travel between arteries and vein complexes, such as those in the splenic nerve or the renal nerve among others.

In some embodiments, a method of recording and stimulating a peripheral nerve may include exposing and isolating a target nerve from the surrounding tissue, engaging an implantable electrode to the target nerve by at least one of passing the implantable electrode about the exposed target nerve and forming a knot with implantable electrode, and inserting the implantable electrode through the epineurium of the exposed target nerve, wherein the implantable electrode further comprises a multi-layer graphene-fiber core, an insulative coating surrounding the multi-layer graphene fiber core, and a metal layer disposed between the multi-layer graphene-fiber core and the insulative coating; and at least one of recording and stimulating from the peripheral nerve. Optionally, engaging a peripheral nerve may include implanting the implantable electrode inside the peripheral nerve, sutured through the peripheral nerve, or over the peripheral nerve. Optionally, the peripheral nerve may be peripheral to at least one of the heart, lungs, stomach, liver, spleen, pancreas and pelvic organs.

BRIEF DESCRIPTION OF THE DRAWINGS

The patent or application file contains at least one drawing executed in color. Copies of this patent or patent application with color drawing(s) will be provided by the Office upon request and payment of the necessary fee.

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

The present disclosure relates to the making and bioelectronics applications of metallized graphene fibers. In some embodiments, the graphene fibers may be coated with platinum, and used to record and stimulate from one or more tissues and organs. In some embodiments, the fabrication of flexible and free-standing graphene-fiber based microelectrode arrays with a thin metal (i.e., platinum) coating, as a charge collector, results in a structure with low impedance, high surface area and excellent electrochemical properties. In comparison with conventional graphene electrodes or platinum (Pt) electrodes, the hybrid platinized graphene fibers discussed herein may be robust and provide better performance. In particular, embodiments of microelectrode arrays built in accordance with the disclosure herein may include low impedance and porous structure of graphene fiber with a thin platinum layer thereupon. The graphene fiber may provide for an unrivaled charge injection capacity and the ability to record and detect neuronal activity, while the thin Pt layer transfers the collected electrons along the microelectrode efficiently. Accordingly, the microelectrodes may be capable of detecting neuronal activity with a high signal to noise ratio.

A major drawback of conventional free-standing carbon nanotubes and graphene microfibers lies in the high resistivity compared with their metallic counterparts. When a microelectrode is longer than a few millimeters, the resistivity increases significantly, which poses a significant challenge to low noise recording. By contrast, a system built in accordance with the present disclosure may overcome this limitation by applying a thin coating of metal (e.g., platinum in the range of 200 nm) as the current collector on the wet-spun graphene microfibers. This modification integrates the electrochemical characteristics of graphene and electronic properties of the metal to the microelectrodes, without limiting its mechanical flexibility and high surface area. The low impedance and porous structure of graphene fiber result in an unrivaled charge injection capacity with the ability to record and detect neuronal activity, while the thin metal layer transfers the recorded electrons along the microelectrode efficiently.

Figure 1A:
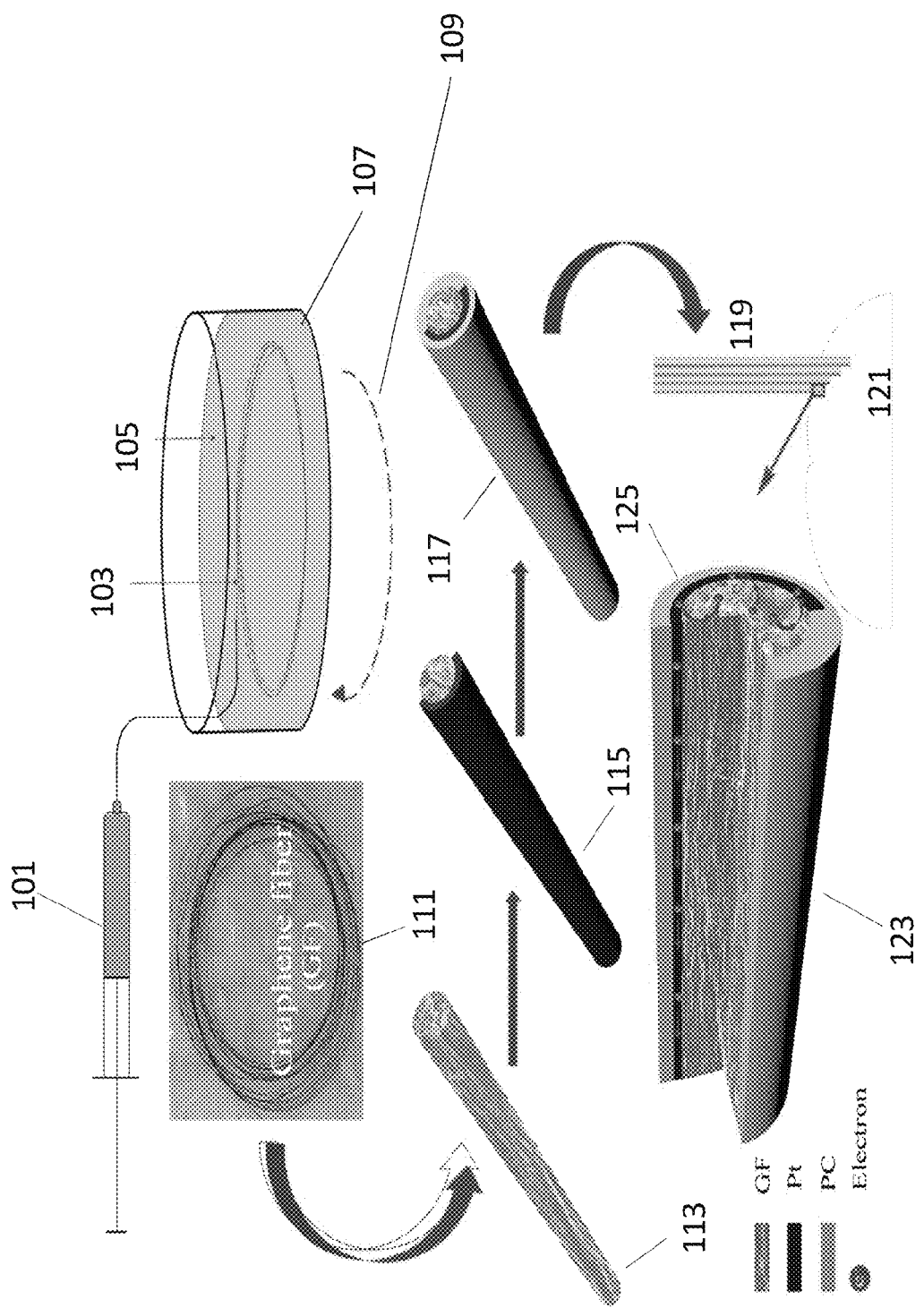
FIG. 1A provides a schematic diagram for making and applying a metallized graphene fiber in accordance with some embodiments of the present disclosure.

FIG. 1A provides a schematic diagram of a process for manufacturing a metallized graphene fiber microelectrode and implanting the microelectrode in the brain. In particular, at 101, liquid crystal graphene oxide (LCGO) process is used to generate graphene oxide fibers 103 which are deposited within an acid bath 105. The bath may be rotated 109 and results in production of graphene fibers (GF) 111.

The GF may be cut into smaller pieces 113 and coated by a metal to form a metal-coated graphene fiber 115. The metal-coated graphene fiber 117 may then be covered by an insulating material. The insulating material may then be cut such that one conducting surface and/or a sharp tip is exposed for recording and/or stimulation. One or more insulated metal-coated graphene fibers may be assembled 119 and implanted into a brain 121. A cross-sectional view 123 illustrates the movement of electrons 125 through the metal layer of the insulated metal-coated graphene fiber.

Figure 1B:
FIG. 1B provides a flowchart for a process of making a metallized graphene fiber in accordance with some embodiments of the present disclosure.

FIG. 1B provides a flowchart illustrating the method for manufacturing a metallized graphene fiber microelectrode. In a first step 1125, graphene fibers (GF) are fabricated using wet-spun liquid crystal graphene oxide (LCGO) process. Description of the process for fabricating GF using LCGO, and further Solid State Exfoliation of Graphite is described in Esrafilzadeh, D., Jalili, R., Stewart, E. M., Aboutalebi, S. H., Razal, J. M., Moulton, S. E. & Wallace, G. G. (2016). High-performance multifunctional graphene-PLGA fibers: toward biomimetic and conducting 3D scaffolds. Advanced Functional Materials, 26 (18), 3105-3117, which is hereby incorporated by reference in its entirety. In a second step 1127, the fabricated GF are reduced in an acid bath. In a third step 1129, a metallic layer is deposited over at least a portion of the individual GF filaments. In a fourth step 1131, the GF filaments (with the deposited metallic layer) is cut into individual pieces and attached to conductive wires. In a fifth step 1133, the individual pieces are coated with an insulative material. In a sixth step 1135, active sites of the microelectrode including the GF filaments are exposed 1135.

In some embodiments, the GF fibers do not include a binder material. In some embodiments, the GF core may have a diameter in the range of between about 10 μm to about 200 μm. Embodiments where the GF fiber does not include a binder may be manufactured at less cost and provide better performance, as conventional binders may be detrimental to the electronic and electrochemical properties of the structure, as they aid the processing of mechanically support the structure.

In some embodiments, the insulative coating may be a polymer-based coating, such as Parylene-C. The insulative coating may have a thickness of about 2 μm.

In some embodiments, the metal layer may be sputtered onto the surface of the graphene fiber core. In such an embodiment, the metal layer may cover all or a portion of the graphene fiber core. In some embodiments, the metal layer may cover half the surface area of the graphene-fiber core. The metal layer may include one or more of platinum, iridium, iridium oxide, platinum-iridium, and titanium nitride. In some embodiments, the metal layer has a thickness in the range between about 10 nm to about 500 nm. In some embodiments, the metal layer may cover between about 50% to 75% of the surface area of the graphene fiber core. The percentage of the surface area covered by the metal layer may be adjusted for manufacturing processes.

Further, as illustrated in FIG. 1B, the multi-layered graphene fiber core may be formed by performing an in-situ reduction of highly-ordered graphene oxide sheets in a liquid crystalline. Optionally, this may include the step of wet-spinning liquid crystalline dispersions of graphene oxide using a coagulation bath containing an acid. In some embodiments, the acid may be hypophosphorous acid and/or calcium chloride.

In some embodiments, graphene fibers may be generated by producing single sheets of graphene oxide comprising 2 micrometers having superior flexibility. A less conductive metal, such as platinum, may then be used to metalize the graphene fibers. However, the metal layer may be used to improve overall conductivity by collecting the charges.

In some embodiments, the graphene fibers built in accordance with the systems and methods described herein may form a multitude of shapes, including but not limited to a mesh structure, an array, thread, yarns, sharpened needle, and the like. Alternatively, the graphene structures may be bioprinted into any suitable shape for recording and/or stimulating.

Fabrication, characterization, and bioelectronic application of metallized graphene fibers built in accordance with the disclosure above, are provided in the examples below.

EXAMPLES

Example 1

High-Performance Graphene-Fiber-Based Neural Recording Microelectrodes

The foregoing example demonstrates the fabrication, characterization, and acute in-vivo performance of a flexible and free-standing microelectrode made from graphene fibers coated with Pt for neural stimulation and recording applications in accordance with the disclosure above. Taking advantage of the unique combination of high mechanical strength and high bending flexibility of GO, robust, flexible fibers and highly conductive electrodes were fabricated. The resulting graphene fiber-platinum coated (GF-Pt) microelectrodes have superior electrochemical properties and are characterized by remarkably lower impedance and higher charge storage capacity. Voltage transient analysis confirmed that these microelectrodes have high charge injection capacity of over 10 mC/cm$^2$. For in-vivo applications, a high signal to noise ratio (SNR) of 7.10 dB for the microelectrode array and 9.2 dB for a single microelectrode was achieved during neural recording. Pt-coated graphene fibers seem to be an advantageous material for developing the next generation neural stimulation and recording microelectrodes with neural-scale size, low impedance, high charge injection capacity, and high flexibility, thus affording closed-loop, bidirectional implantable devices.

Electrode Fabrication

In accordance with the methods and techniques described above, the high mechanical strength and super flexibility of graphene oxide sheets allowed for the direct processing of three-dimensional (3D) structures without the need of any binder to aid the processing. To achieve self-assembled, multi-layer, binder-free, aligned microfibers with reduced graphene sheets, wet-spinning of liquid crystalline dispersions of graphene oxide (LCGO) was conducted using a coagulation bath containing hypophosphorous acid. This coagulation bath reduced the GO during the spinning process without compromising the flexibility and mechanical strength. Flexibility of a microfiber is an important characteristic for fabricating implantable microelectrode, as it minimizes foreign body reaction and maximizes greater proximal neuron survival in comparison with traditional metal electrodes.

More particularly, GFs were fabricated via a wet-spinning process from home-made LCGO. The fabricated wet LCGO fibers were reduced with hypophosphorous acid solution (50% in water, Sigma-Aldrich) at 80° C. for 24 h. The dried individual GF filaments (40 μm diameter) were deposited with a 200 nm Pt layer by using a sputter coater to make GF-Pts. The prepared GF-Pts were cut into 8-12 mm pieces and attached to silver wires using conductive silver paint (SPI supplies, Z05002-AB). Then the GF-Pts along with silver wires were coated with Parylene C using a Parylene deposition system coater (Specialty Coating System, PDS 2010 Labcoater). The assembled GF-Pt-PCs were dipped into liquid nitrogen for about 10 min and the active sites of a microelectrode were exposed by cutting its tip with a sharp scissors. The Parlyene C on the tail of the silver wire was removed before test to make it conductive. Electrical conductivity of fibers was measured using a home-made four-point probe conductivity set-up with 240 um probe spacing using a galvanostat current source (Princeton Applied Research 363) and a digital multimeter (Agilent 34401A). As-prepared fibers and electrodes were directly examined by scanning electron microscopy (JEOL JSM-7500FA) and video microscope (Leica M2056A).

Figure 2:
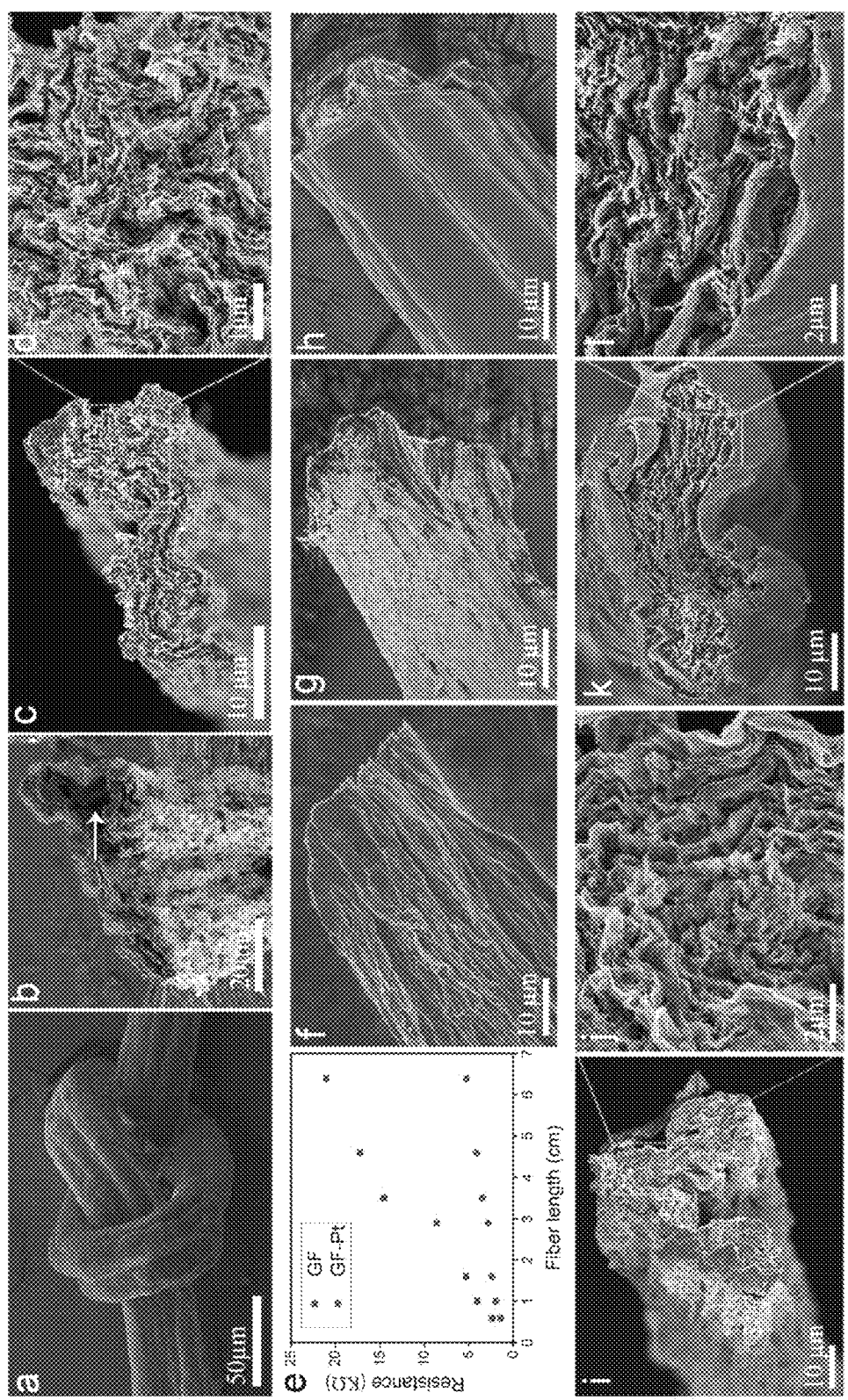
FIG. 2 provides a scanning electrode characterization of a metallized graphene fiber electrode built in accordance with some embodiments of the present disclosure.

FIG. 2 illustrates the flexibility of these graphene microfibers. As illustrated in Panel A of FIG. 2, the graphene microfibers are flexible enough to tie an overhand knot 201. Panels B and C of FIG. 2 illustrate scanning electron microscope (SEM) imagery of graphene microfibers having a diameter of 20±3 µm to 40±5 µm, respectively, by using 19-23 gauge nozzles, respectively. Comparison between the cross-sections of these fibers suggests that those with larger diameters tend to form more irregular shapes with intersheet spaces after drying (as illustrated by the void in a typical fiber of larger diameter indicated by arrow in Panel B of FIG. 2). This may be indicative of severe shrinkage during the drying process, which in turn, could explain the higher conductivity of the 20±3 µm fibers (205±16 S/cm) compared with 52±0.3 S/cm for the 40±5 µm.

Panel D of FIG. 2 illustrates an enlarged SEM cross-section from Panel C of FIG. 2, and shows aligned and highly organized characteristic features of graphene microfibers. Hundreds of individual graphene sheets are collapsed together during the coagulation bath creating a multi-layer core in the graphene fiber assembly. Higher magnification SEM image of the cross-section of a typical fiber presented in Panel D of FIG. 2 shows a particularly aligned feature of the graphene sheet layers. Here, the in-situ reduction of fully ordered multi-layered GO sheets in liquid crystalline state inhibited the randomization of the morphology by preventing the relaxation phase. In fact, the inherent LC order was maintained allowing the highly organized assembly of GO microfibers. Furthermore, the in-situ reduction constrained any uncontrolled re-stacking of the sheets. Consequently, a fully ordered and porous architecture was obtained. Such reduced graphene fibers provided an extremely high surface area of up to ~2210 $m^2$ $g^{-1}$ that facilitated the accessibility of electrolyte and ionic diffusion into the resultant electrode.

Panel E of FIG. 2 illustrates the electrical resistivity of graphene microfibers as a function of platinum coating and length. As illustrated, the resistance increases with fiber length. Further, GF-Pt electrodes illustrate lower resistance than GF electrodes. The electric resistance of these microfibers was affected by their length, which increased from ~2 to 20 kΩ as the length increased from ~0.5 to 5 cm. To minimize the effect of the fiber length on the resistivity and facilitate the recording of fine nerve's signals, one side of the microfibers was sputter coated with up to ~200 nm thick layer of Pt (GF-Pt). The Pt coating resulted in a significant increase in the conductivity from 205±16 S/cm to 460±30.3 S/cm. Moreover, as Pt acts as current collector, the increase in the resistivity due to the length of microfibers became considerably less detrimental. Minimization of the resistivity is particularly desirable to achieve noise reduction, stability of recordings and effective electrical stimulation.

Microelectrodes were fabricated by insulating each individual platinized microfiber with an insulating polymer coating of ~2 µm (Parylene-C, GF-Pt-PC), before a sharp cut of the tip in a liquid nitrogen bath; leaving only the tip exposed as an electrochemically active site. Parylene-C was selected due to its high dielectric property, biocompatibility, pin-hole free and uniform coatings, and its common use for neural prostheses. Microelectrodes made from bare graphene fiber (i.e., no Pt coating) were fabricated for comparison. Moreover, while the polymer coating process increased the robustness of the graphene microfibers, the flexibility was also improved as demonstrated by tying an overhand knot.

Panels F, G, and H of FIG. 2 show SEM images of a typical microfiber after each coating step. In particular, Panel F is an SEM image of the outer surface of a GF electrode. Panel G is an SEM image of the outer surface of a GF electrode coated with Pt. Panel H is an SEM image of the outer surface of a GF electrode coated with Pt and insulated with Parlyene-C. Both Pt and Parylene-C coatings formed thin layers around the microfibers, retaining the porous structure and high surface area at the tip, as evidenced by high-resolution SEM microscopy images (see Panels I, J, K, and L of FIG. 2). The high surface area results in high recording sensitivity, and a large charge injection capacity with low impedance at 1 Hz to 10 kHz. In particular, Panels I and J illustrate a cross-sectional SEM image of GF-Pt electrodes, and Panels K and L illustrate SEM images of the tip of the final microelectrode.

Electrochemical Characterization

Figure 3:
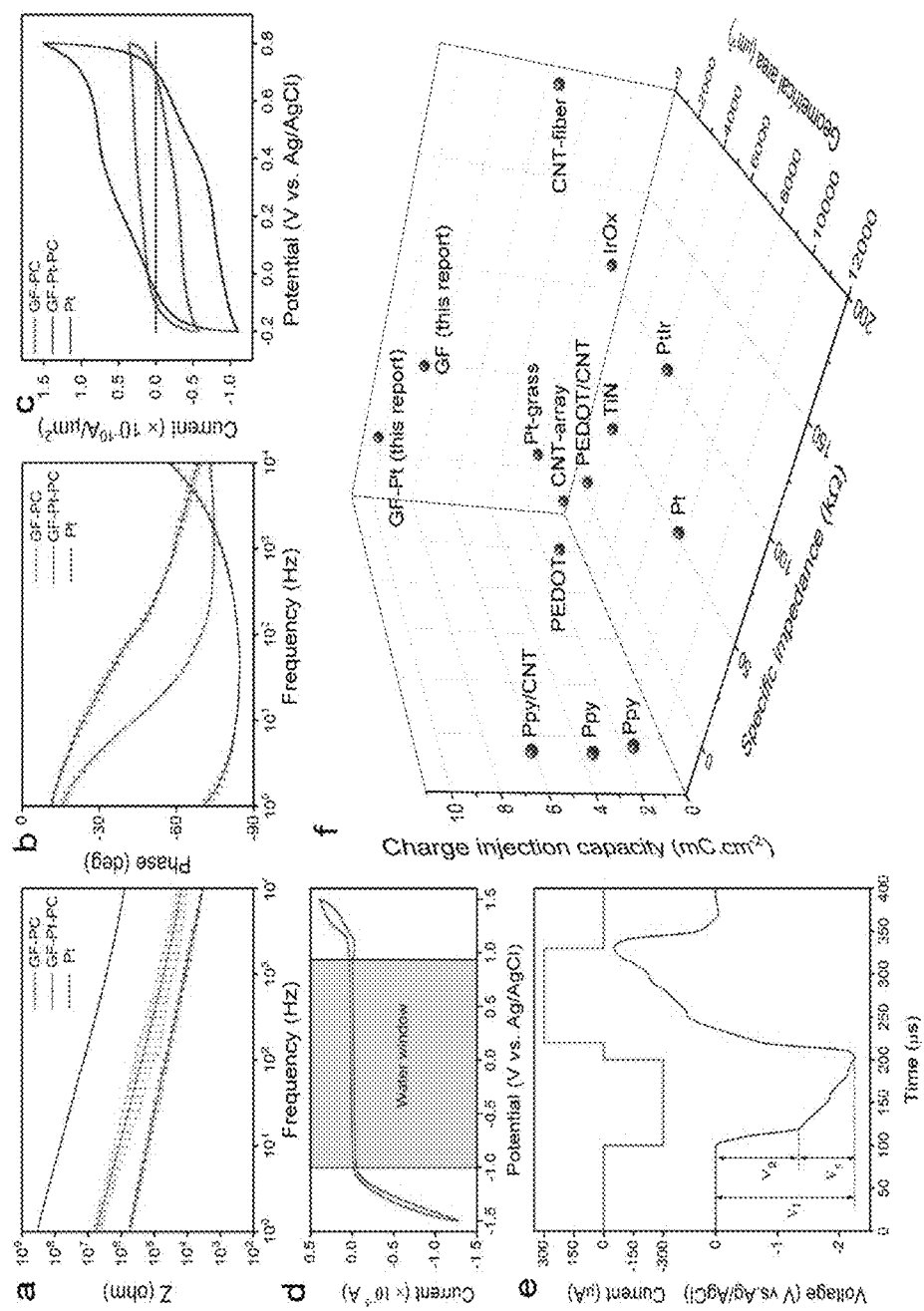
FIG. 3 provides a electrochemical characterization of a metallized graphene fiber electrode built in accordance with some embodiments of the present disclosure.

During the stimulation and recording of bioelectric actions, the electrode carries out the function of transduction from the ionic currents in the electrolyte into an electric current in the measurement system. High electrical impedance of the interface between electrode and living tissue can negatively impact the signal-to-noise ratio and increase signal distortion. This particularly becomes very important for microelectrodes due to the reduced dimensions. FIG. 3 illustrates the electrochemical performance of the graphene microelectrodes as evaluated by electrochemical impedance spectroscopy (EIS), cyclic voltammetry (CV), and calculations of charge storage capacity and charge injection limit.

Electrochemical impedance spectroscopy (EIS) and Cyclic voltammetry (CV) were performed with a CHI 660E electrochemical workstation (CH Instruments) in phosphate buffered saline (PBS, pH 7.4, Sigma-Aldrich) at room temperature. A three-electrode cell system was employed with the test sample as working electrode, a platinum sheet as counter electrode, and Ag|AgCl as reference electrode. CVs were recorded between the voltages of −0.2 and 0.8 V at scan rates of 10-50000 mV/s. Each sample was tested for 3-5 cycles, and the cathodic charge storage capacity was calculated from the integration of current over time recorded in the last cycle at scan rate of 100 mV/s. Sweeps from −1.6 to 1.6 V were performed to determine the water window (e.g., threshold to electrolysis) of GF-Pt-PC electrodes, and the water oxidation and reduction potentials were determined when the sharp current peaks were detected. EIS was performed between frequencies of 1-$10^4$ Hz, and the specific impedance was calculated at $10^3$ Hz.

Panel A of FIG. 3 illustrates the modulus of impedance of microelectrodes. An electrode made from Pt wire of similar diameter with microfibers was also fabricated and tested as the control. EIS analysis showed that the impedance of graphene microelectrodes was ~2 orders of magnitude lower than the Pt electrode in the range of frequencies tested (1 Hz to 10 kHz, Panel A). Particularly, the impedance at 1 kHz was over 50 times lower than the Pt electrode (~50 kΩ vs ~300 kΩ). This large reduction in the impedance of the graphene microelectrodes was as a result of the increased available surface area of fully ordered and separated graphene sheets. Furthermore, the impedance of the Pt modified microelectrodes (at 1 kHz) was ~5 and ~300 times lower than neat graphene and Pt microelectrodes, respectively. Adding a thin layer of Pt on the graphene microfiber (as current collector) resulted in a strong synergistic effect leading to a robust and superior hybrid microelectrode with lower impedance.

Panel B of FIG. 3 illustrates the phase angle of impedance of microelectrodes. At an ideally polarizable electrode during the stimulation, the charge passed would be completely attributed to the capacitance rather than any Faradic reaction. The phase lag of microelectrodes, as illustrated in Panel B of FIG. 3, indicates that the electrochemical interaction at the exposed tip is controlled by a capacitive charging-discharging process over the double layer of the microelectrode tip (an adsorption controlled process).

Panel C of FIG. 3 illustrates CVs of the microelectrodes at 10 mV/s in PBS solution. CV is a simple and fast technique for measuring the capacitance and Faradaic components at an electrode-solution interface. Panel C of FIG. 3 compares cyclic voltammetry (CV) of different electrodes prepared in this example. Although, both graphene-based microelectrodes showed near-rectangular CV curves, the current of the Pt modified microelectrode was significantly higher than other electrodes. This improvement was due to integration of high conductivity of Pt coating coupled with the high surface area of the GO electrode that allows effective diffusion of electrolyte ions, followed by a facile electron transfer via the Pt layer. Furthermore, the cathodic charge storage capacity of the Pt modified GO microelectrode, calculated from the CV, was 946±140 mC/cm², a value of ~3 orders of magnitudes higher than Pt electrode and ~2 times higher than the unmodified graphene microfibers.

Panel D of FIG. 3 illustrates the water window of microelectrodes, and Panel E of FIG. 3 illustrates the voltage transient test of microelectrodes. And Panel F of FIG. 3 illustrates a comparison of the charge injection capacity, specific impedance, and geometrical area of a microelectrode built in accordance with the methods described herein in comparison with neural interface electrodes reported in literature.

In particular, the voltage transient measurement was performed on a two-electrodes set-up in PBS solution (pH 7.4, Sigma-Aldrich) at room temperature. A symmetric charge-balanced, cathodic first, biphasic current pulse with 100 µs width, 20 µs interphase open circuit potential and 2.78 ms short circuit at 250 Hz was generated by a digital stimulator DS800 and A365 Isolator units (World Precision Instruments). The voltage waveform across the active microelectrode in response to the applied current pulse was recorded with an e-corder system (eDAQ). The maximum negative polarization potential ($E_{mc}$) was calculated by subtracting the initial access voltage ($V_a$) from the total voltage transient. The charge injection capacity was determined when $E_{mc}$ reached the water reduction limit from the following equation:

$$Q_{inj} = \frac{I_c \cdot t_c}{GSA},$$

where $Q_{inj}$ is the charge injection limit capacity, $I_c$ is the current pulse applied, $t_c$ is the pulse width, and GSA is the geometric surface area.

Electrical stimulation initiates a functional response by depolarizing the membranes of excitable cells, which is achieved by the flow of ionic current between the electrodes. Voltage transient measurements were made to determine the maximum positive and negative polarization values across the electrode-electrolyte interface, and estimate the maximum charge that can be injected in a stimulation pulse without exceeding the water electrolysis limit. The potential is swept over a wide window to obtain the voltage range where the electrode, electrolyte and water are neither oxidised nor reduced. To ensure the safe polarization of the microelectrode during stimulation, a CV of the microelectrode was recorded by sweeping the potential between the voltage limits of −1.6 V to 1.6 V (vs. Ag/AgCl electrode). In biological systems, this potential range is largely determined by the oxidation and reduction of water (water window). The water window was limited by the water oxidation and reduction voltages, indicated by a steep increase in the current. In this example, the water window of GF based microelectrodes was found between −1.0 V to 0.9 V (Panel D of FIG. 3). The upper portion of Panel E of FIG. 3 shows a typical input biphasic current pulse (300 µA and 20 µs delay). The potential excursion response (see lower portion of Panel E of FIG. 3) to the current pulse shows an initial, rapid change in potential, known as the access voltage ($V_a$=−1.35 V), due to the ohmic resistance of the electrolyte, followed by a slowly rising polarization voltage ($V_p$=−0.90 v), which is due to the charging of the electrode/electrolyte interface. The Vp was calculated by subtracting the Va from the maximum negative voltage in the transient ($V_t$=−2.25 V).

The polarization voltage of phase one of the biphasic pulse was used to determine the charge injection limit and obtained by continuously increasing the current amplitude until the polarization voltage reached 1.0 V. The charge injection capacity was calculated at $V_p$=0.90 V, before the water reduction potential (Panel E of FIG. 3), to be 10.34±1.5 mC/cm² in the GF-Pt electrode, a value ~3 orders of magnitudes higher than Pt and ~2 times larger than the unmodified graphene micro fibers.

The charge injection capacity of the GF-Pt microelectrode was significantly higher than all of the best reported electrode materials; including but not limited to Pt, carbon nanotube fibers, conducting polymer coatings, metal nitride and oxides, as presented in Panel F of FIG. 3. The synergistic effect of ordered graphene sheets with low electrical resistivity of Pt layer resulted in this remarkable charge injection capacity along with significantly enhanced electrochemical performance.

Durability Characterizations

Figure 4:
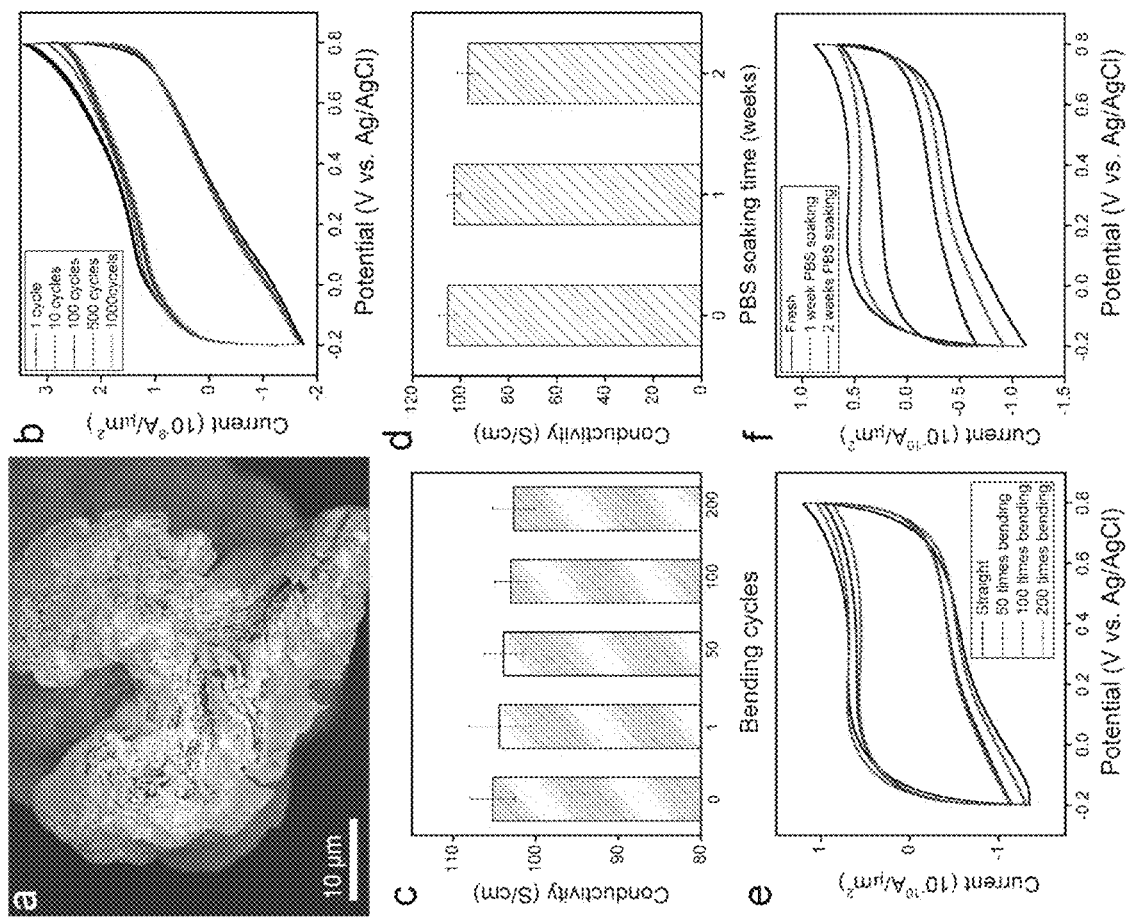
FIG. 4 provides a mechanical and accelerating aging characterization of a metallized graphene fiber electrode built in accordance with some embodiments of the present disclosure.

FIG. 4 illustrates the durability of electrodes built in accordance with the methods described herein. Over time, chronically implanted electrodes are adversely affected by material degradation, and delamination of the insulator coatings such as Parylene, which contribute to device failure. The longevity of the GF-Pt microelectrodes was tested using cyclic voltammetry in PBS solution. Panel A of FIG. 4 shows a representative SEM image of a microelectrode after 1000 electrochemical cycles at a scan rate of 50 mV/s. As illustrated, the electrode tip did not show any noticeable graphene degradation or Parylene delamination. Parylene coating often peels off from rigid underlying electrodes such as Pt and silicon. However, here, the strong interfacial adhesion between the Parylene and graphene microfibers, along with the flexibility and softness of the underlying fiber, resulted in a remarkable stability of the Parylene coating.

Panel B of FIG. 4 confirms that there was no noticeable change in the electrochemical performance over the prolonged stability test.

Furthermore, the stability of graphene microfibers and the microelectrodes were evaluated against repeated bending and prolonged soaking in PBS solution (as illustrated in Panels C, D, E, and F of FIG. 4). In particular, Panel C of FIG. 4 demonstrates that the graphene microfibers show outstanding stability over the bending cycle test, as there was neither obvious difference in conductance between straight and bended GF-Pt fiber electrodes (105.2±2.7 vs 104.4±3.7 S/cm), nor after 200 times bending (105.2±2.7 vs 102.7±2.5 S/cm). Further, Panel D of FIG. 4 illustrates that even after soaking in PBS for 2 weeks, only ~8% conductivity loss was observed. The microelectrodes also could maintain 77.6% and 52.2% charge storage capacity after very tough durability and fatigue tests involving consecutive 200 times 360° folding (Panel E of FIG. 4) and 2 weeks soaking in PBS (Panel F of FIG. 4), respectively.

The electrochemical performance of neural interfacing electrodes of Example 1, which include a microelectrode built in accordance with embodiments of the present disclosure, may be summarized as follows:

| Material | Geometrical surface area ($\mu m^2$) | Impedance (k$\Omega$ at 1 kHz) | Specific impedance capacity (M$\Omega$ $\mu m^2$) | Charge storage capacity (mC/cm$^2$) | Charge injection (mC/cm$^2$) |
|---|---|---|---|---|---|
| Graphene fiber (GF) | 169 ± 25 | 50 ± 7.5 | 19.5 ± 2.9 | 798 ± 110 | 8.7 ± 1.3 |
| Pt coated fiber (GF-Pt) | | 10 ± 1.3 | 11 ± 1.5 | 946 ± 140 | 10.5 ± 1.5 |

Surgical (In-Vivo) Implantation and Neural Activity Recording

In connection with Example 1, electrodes built in accordance with the present disclosure were surgically implanted into rats.

All procedures were performed in accordance to an animal use protocol 15-19 approved by the Institutional Animal Care and Use Committee at the University of Texas at Dallas on the 6$^{th}$ of Jan. 2017. A Long-Evans rat was selected for this study, and the target was within the motor cortex in the region associated with the control of the left forepaw. The animal was anesthetized using 2% isoflurane mixed in oxygen, which was followed by intraperitoneal administration of a cohort consisting of ketamine (65 mg/kg), xylazine (13.33 mg/kg), and acepromazine (1.5 mg/kg). The animal was mounted into a Kopf Model 900 small animal stereotaxic instrument (David Kopf Instruments, CA, United States). Dexamethasone (2 mg/kg) was administered subcutaneously over the shoulders to reduce the inflammatory response and was followed by the subcutaneous administration of 0.5% lidocaine (0.16 cc) directly under the scalp incision site. After exposing the skull, a 2.0 mm by 2.0 mm craniotomy was created with a center at our initial coordinates of implantation of 2.5 mm rostral and 2.5 mm lateral from bregma. The dura in the area was reflected using a dura pick followed by micro scissors to expose the surface of the cortex. The entire area was kept under liquid with frequent application of 7.4 pH sterile physiological phosphate buffered solution.

Five implants were selected for this proof-of-concept study. The first implant consisted of a bundle of four, 40 µm diameter microelectrodes composed of graphitic fibers coated with a thin layer of platinum and encapsulated with Parylene-C insulation (GF-Pt-PC). The second microelectrode consisted of a single, 40 µm diameter graphitic fiber conductor encapsulated with Parylene-C insulator (GF-PC). The third microelectrode was a single, 40 µm diameter GF-Pt-PC microelectrode. The final two microelectrodes consisted one GF-PC and one GF-Pt-PC with 20 µm diameters.

The bundle of four microelectrodes was loaded into a Model 2650 hydraulic micropositioner (David Kopf Instruments, CA, United States) into the microelectrode holder. The tips of the microfiber wire bundle were lowered until they came into contact with the cortical surface at the implantation coordinates, the distance counter on the micropositioner was reset and the device was lowered into the motor cortex at a speed of 1000 µm/s. If buckling of the wire began, the implantation was immediately stopped and the speed was reduced to 100 µm/s. A sterile stainless steel hypodermic needle was inserted into the rat tail to serve as the counter electrode. The optimal implantation depth was 1500 µm.

Each acute recording was performed for at least 10 minutes using an OmniPlex D Neural Data Acquisition System (Plexon Inc., TX, United States). If no single neural units were acquired, we increased the depth of implantation by 200 µm and performed another recording. We continued to increase the depth of implantation until a successful recording with single units was acquired, or the wire implant reached a maximum depth of 2000 µm. After the recording, the microfiber wire/bundle was explanted completely from the brain, the micropositioner was disinfected with isopropanol, and another wire was loaded in the micromanipulator. Each additional microfiber microelectrode was implanted at separate locations, with the second implant position located 200 µm rostral from the initial implant location. The third microelectrode was implanted 200 µm lateral from the second location, with the next at 200 µm caudal from the third location, and the last 100 µm from the third. Identical recording procedures were followed for all subsequent microelectrodes. After the investigation, the rat was euthanized using an overdose of 5% isoflurane vapor which was applied until breathing cessation occurred.

The wideband recordings obtained from OmniPlex D were further processed using Plexon's Offline Sorter software. The wideband signals were filtered using a 4$^{th}$ order Butterworth filter with a cutoff located at 550 Hz and common-mode referencing was used to eliminate noise. The threshold to select single units was set to 3σ from peak height with the waveform duration of 1500 µs. Waveforms sorted from the threshold crossing were further evaluated using the software's built-in Valley-Seeking algorithm. The noise envelope was obtained setting the threshold to ±3σ of the original signal and removing the waveform segments 250 ms before and 750 ms after the threshold crossing. The average amplitude of the single unit waveforms was determined by the largest negative deflection from zero crossing. The reported signal-to-noise (SNR) ratio was calculated in decibels using the following formula:

$$SNR = 10\log_{10}\left(\frac{A_{signal}}{A_{noise}}\right)^2.$$

Figure 5:
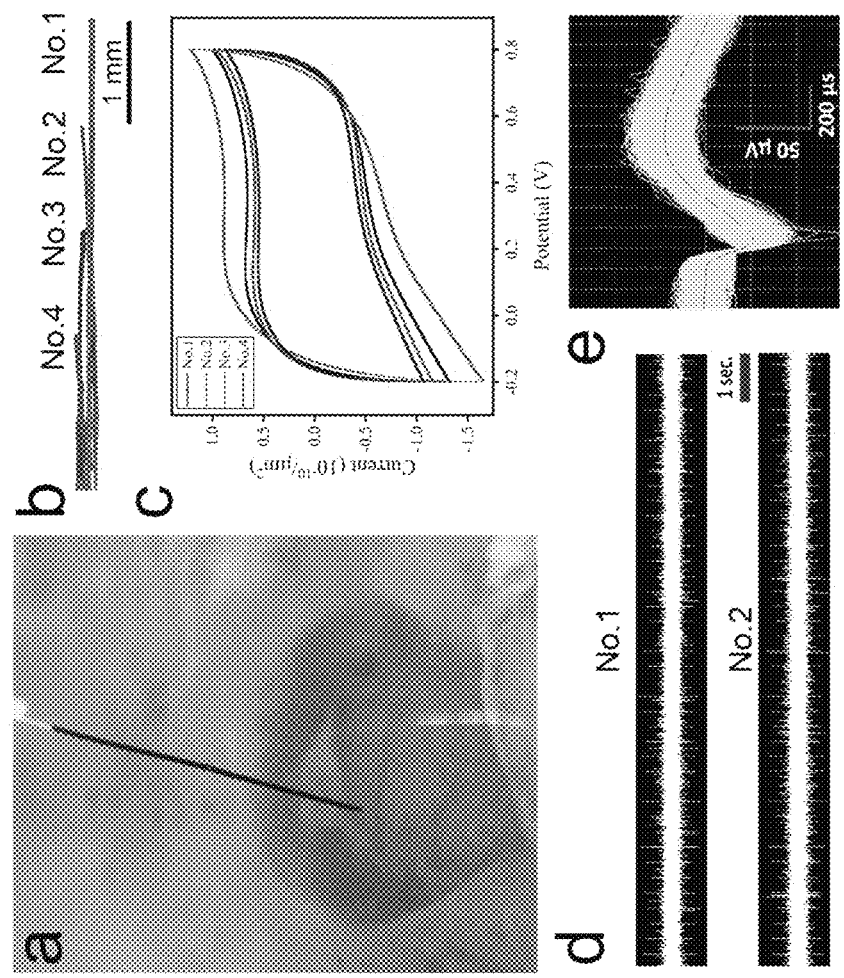
FIG. 5 provides neural activity recorded from the rat brain by a metallized graphene fiber electrode built in accordance with some embodiments of the present disclosure.

To demonstrate proof-of-concept neural recordings in-vivo, first a single microelectrode was implanted in the cerebral cortex of adult rats. Cellular-scale microelectrodes (20 μm to 40 μm) containing fully ordered graphene sheets, provided us with a sufficient mechanical robustness and sharpness to be inserted and precisely positioned to record neural signals for a total of ten minutes. Panel A of FIG. 5 shows an image of the implanted microelectrode. Additionally, the in-vivo test used an array of four tip-exposed microelectrodes, aligned and glued together at approximately 1 mm between the wire tips (as illustrated in Panel B of FIG. 5). Before the in-vivo tests, CV of each individual microelectrode was recorded (as illustrated in Panel C of FIG. 5) to confirm a suitable electrochemical performance. While inserting the bundled microelectrodes, only 3 of the 4 single microelectrodes penetrated into the motor cortex. The fourth microelectrode buckled and subsequently did not enter the brain, so it was eliminated from the recording. Of the three penetrating microelectrodes, two showed single unit activity at a bundle depth of 1500 μm measured from the surface of the cortex. Panel D of FIG. 5 shows 10 seconds of 550 Hx high-pass filtered electrical signals obtained from two of the GF-Pt-PC bundled microelectrodes inserted 1.5 mm into the motor cortex of a Long Evans rat at the location of 2.5 mm rostral and 2.5 mm lateral from bregma. Panel E of FIG. 5 shows 1543 single unit signals obtained over 10 minutes of recording time from one of the GF-Pt-PC implanted microelectrodes. The dark line in the center of the waveforms represents the average single unit signal which has an amplitude of −70.2 μV, and a peak to peak value of 130.5 μV. The units of the second active electrode (not shown), have a similar shape with a slightly lower mean amplitude of −54.3 μV with a peak to peak value of 89.7 μV. The SNR for the two microelectrodes are 7.10 dB and 4.43 dB.

Figure 6:
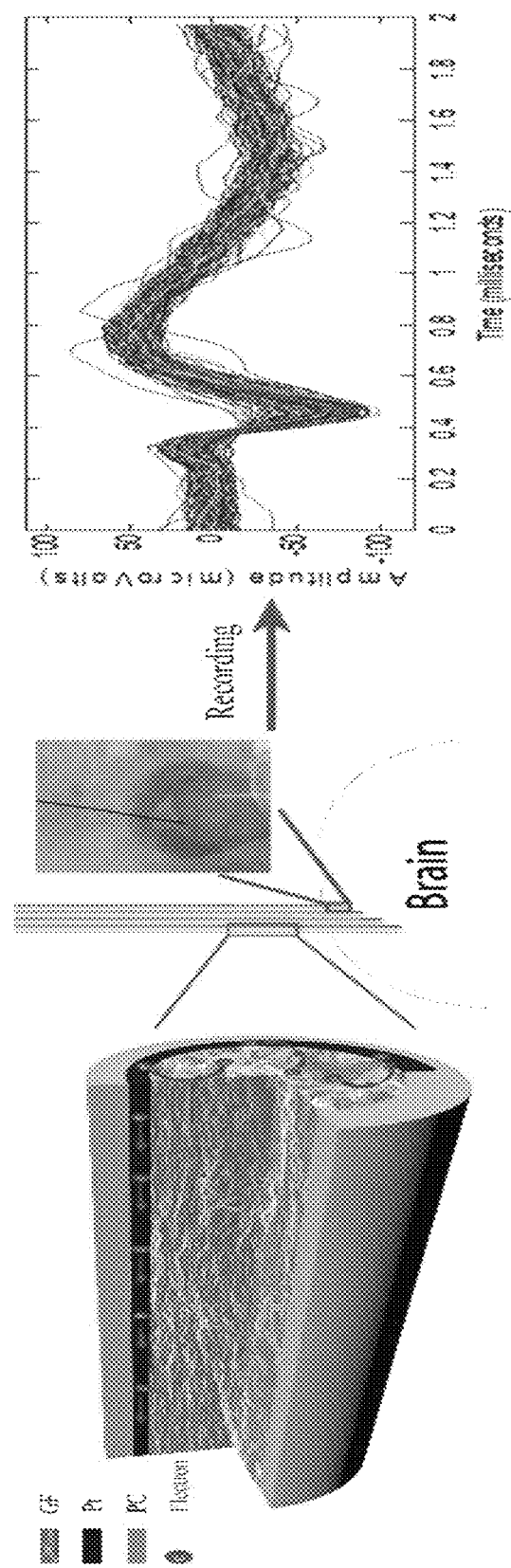
FIG. 6 provides neural activity recorded by a metallized graphene fiber electrode built in accordance with some embodiments of the present disclosure.

As illustrated in FIG. 6, an additional, single GF-Pt microelectrode was implanted to a depth of 1500 μm from the cortical surface, and compared with a GF-only micro-electrode implanted to a depth of 2000 μm. Signals obtained from the single microelectrodes produced single unit waveforms which were similar in both shape and duration as compared to the bundled microelectrodes shown in FIG. 5. The GF-Pt microelectrode displayed two single units of −75.2 μV and −69.3 μV amplitudes, peak-to-peak voltages of 183.4 μV and 123.6 μV, and signal-to-noise ratio (SNR) of 9.2 dB and 8.4 dB respectively. All of our GF-Pt micro-electrode signals have demonstrated recording signals which are larger than previously reported. On the other hand, the GF-only microelectrode showed a weaker performance. Although it possessed a signal amplitude of −93.9 μV and a peak-to-peak voltage of 146.4 μV, the noise was considerably larger which lead to a reduced SNR of 3.0 dB.

Accordingly, the robust, flexible and free-standing graphene-fiber based microelectrode arrays with an extremely thin platinum coating demonstrate high performance neural recording microelectrode with low impedance, high surface area and a high charge injection capacity. In-vivo studies show that microelectrodes implanted in the rat cerebral cortex can detect neuronal activity with remarkably high signal-to-noise ratio (SNR).

Carbon nanotubes and graphene have been successfully demonstrated as an alternative platform to other conductive materials used as neural implant devices, such as platinum, iridium, titanium nitride, and iridium oxide, for effectively capturing neural signals. The example experiments have demonstrated the ability of the platinum modified graphene microfibers for single unit recording capability with high signal-to-noise ratio. Additionally, the recorded units captured by these electrodes were not dissimilar to those reported with other small microelectrode platforms.

Figure 7:
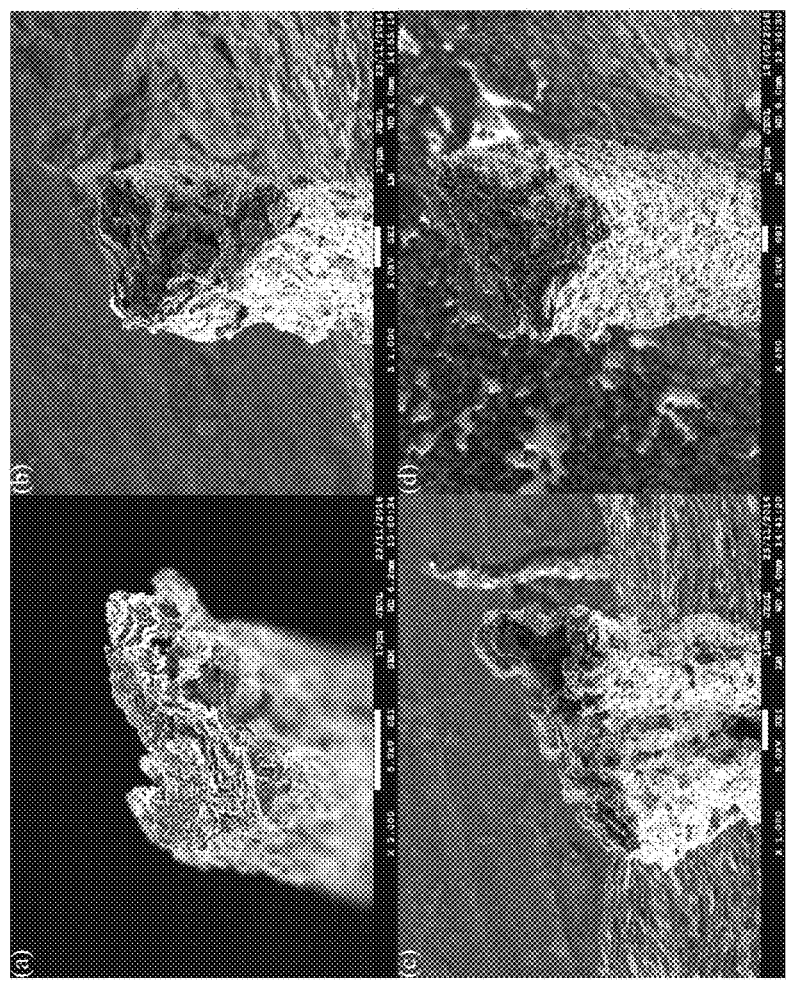
FIG. 7 provides a characterization of a metallized graphene fiber electrode built in accordance with some embodiments of the present disclosure.

FIG. 7 provides SEM imagery of cross-sections of various fibers and illustrates that fibers with larger diameters tend to form larger voids during the trying, due to a larger shrinkage than the smaller fibers.

Figure 8:
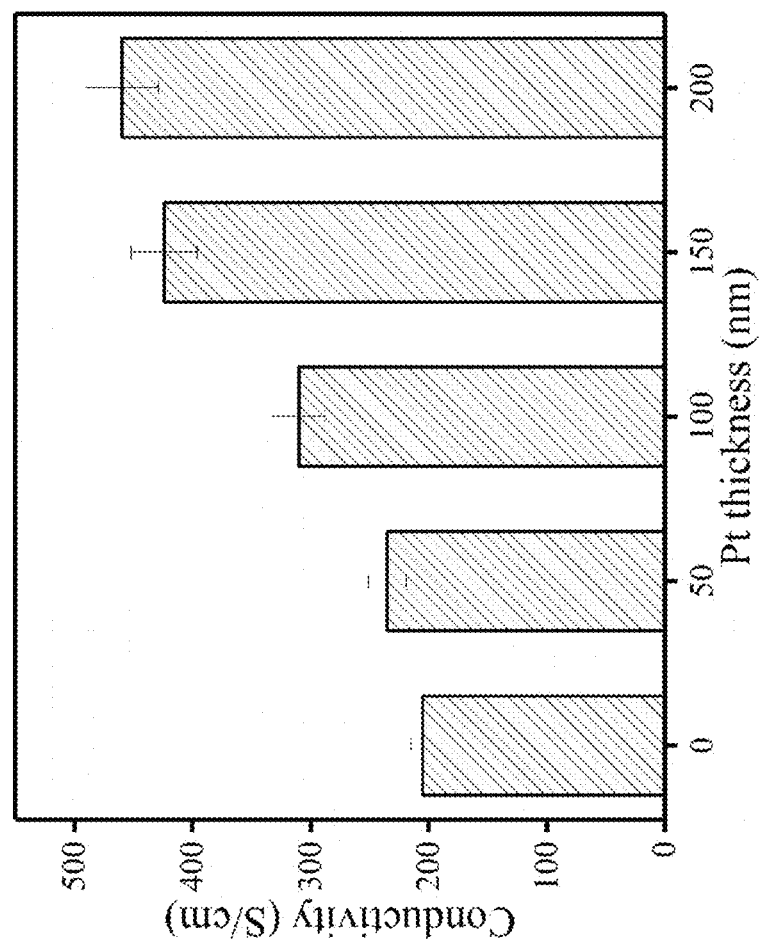
FIG. 8 provides a characterization of a metallized thickness coating on the graphene fiber electrode built in accordance with some embodiments of the present disclosure.

FIG. 8 provides a bar chart illustrating the conductivity of thin graphene fiber with different Pt coating thicknesses.

Figure 9:
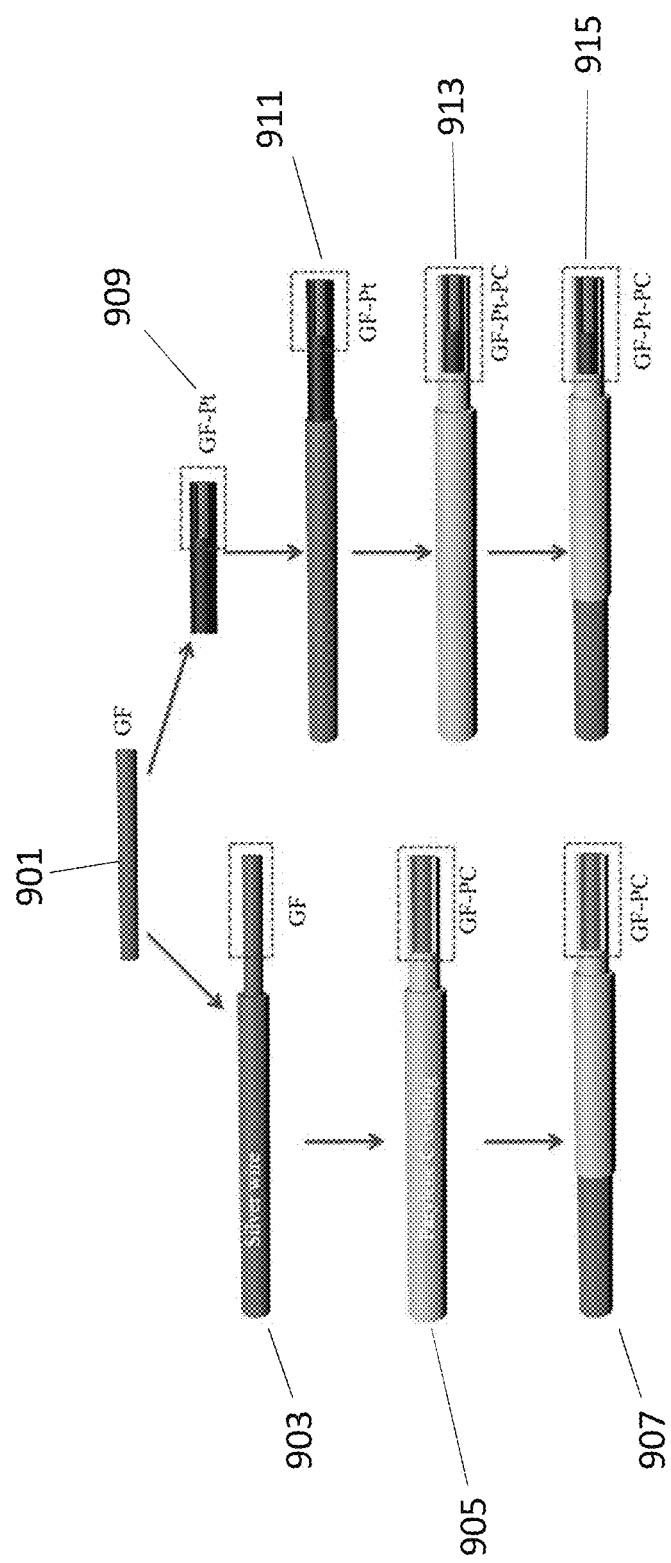
FIG. 9 provides a schematic diagram for making and applying a metallized graphene fiber in accordance with some embodiments of the present disclosure FIG. 10 provides a characterization of a metallized graphene fiber electrode built in accordance with some embodiments of the present disclosure.

FIG. 9 illustrates a process for fabricating microelectrodes with Pt coating (GF-Pt-PC) and without Pt coating (GF-PC). As illustrated in FIG. 9, optionally, a graphene fiber (GF) 901 may be coated with platinum thus forming a microelectrode with Pt Coating (GF-Pt) 909. The GF or GF-Pt may be attached to a silver wire as illustrated at steps 903 and 911, respectively. Additionally, Parylene coating may be applied at steps 905, and 913 respectively. Further, as illustrated at steps 907, and 915, the tips of each microelectrode are exposed and the Parylene C on the silver wire tails are removed for connection.

Figure 10:
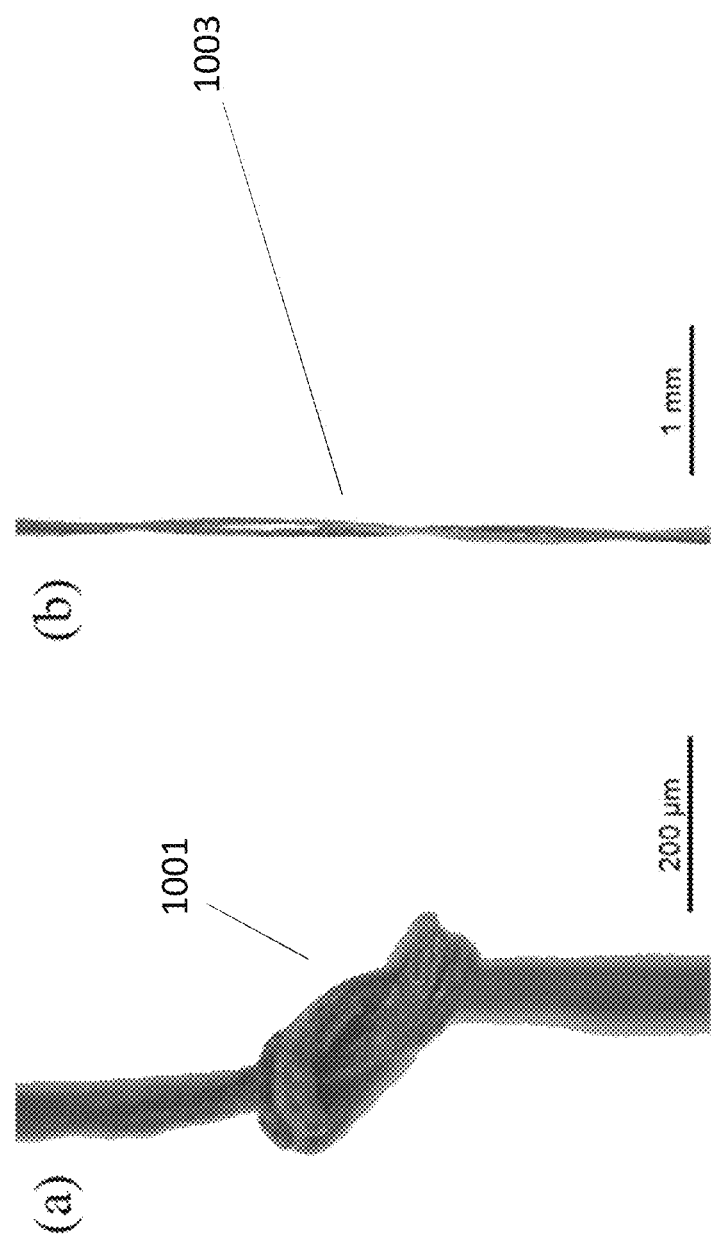

FIG. 10 provides optical microscope images of GF-Pt. As illustrated GF-Pt is very flexible and can be easily knotted 1001 and twined 1003.

Figure 11:
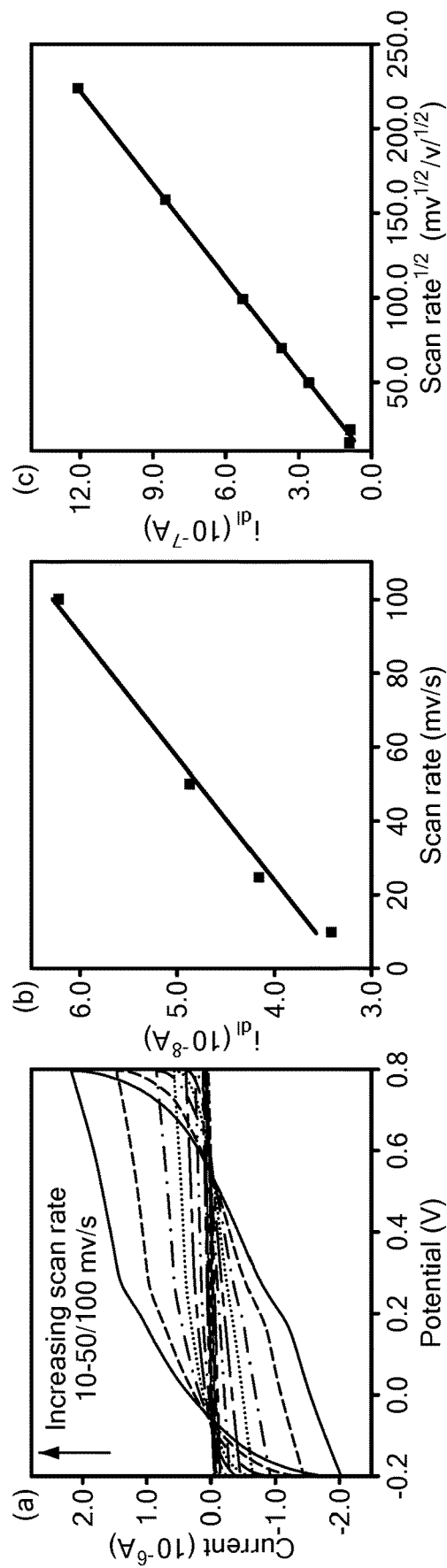
FIG. 11 provides a characterization of a metallized graphene fiber electrode built in accordance with some embodiments of the present disclosure.

FIG. 11 provides additional electrochemical characterization of an electrode built in accordance with the disclosure herein. In particular, Panel A of FIG. 11 provides CV measurement of GF-Pt-PC to determine the dynamic behavior over the double layer of graphene. Additionally, Panel B of FIG. 11, illustrates that the peak current is linearly dependent on scan rate at low scan rate with linear regression equation as y=3.2659*10−8+3.0127x (R2=0.980), suggesting a surface adsorption-controlled process of GF-Pt-PC. Further, Panel C of FIG. 11 illustrates that the peak current is linearly dependent on square root of scan rate at high scan rate with linear regression equation as y=−1.6698*10−8+5.4659x (R2=0.999), suggesting a diffusion-controlled process.

Figure 12:
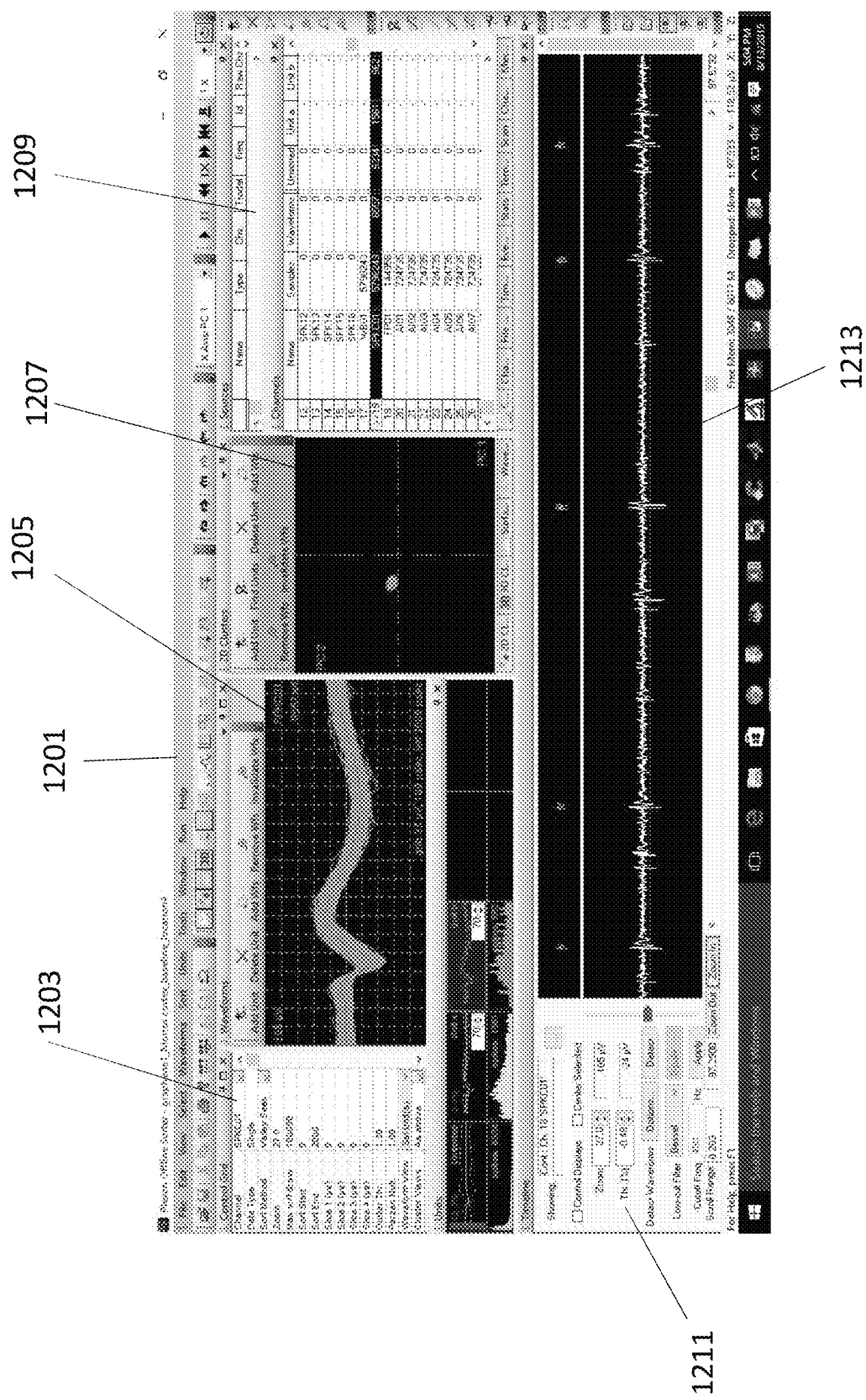
FIG. 12 provides neural activity recorded by a metallized graphene fiber electrode built in accordance with some embodiments of the present disclosure.

FIG. 12 provides a snapshot of the recording process when a single unit was implanted in the cerebral cortex of adult rats. As illustrated, a user may use a graphical user interface 1201 to select recordings from a particular electrode 1203. Further, the graphical user interface 1201 may allow a user to view a waveform 1205, clusters of waveform data 1207, electrode channel information 1209, a timeline 1211, and the waveform 1213.

Figure 13:
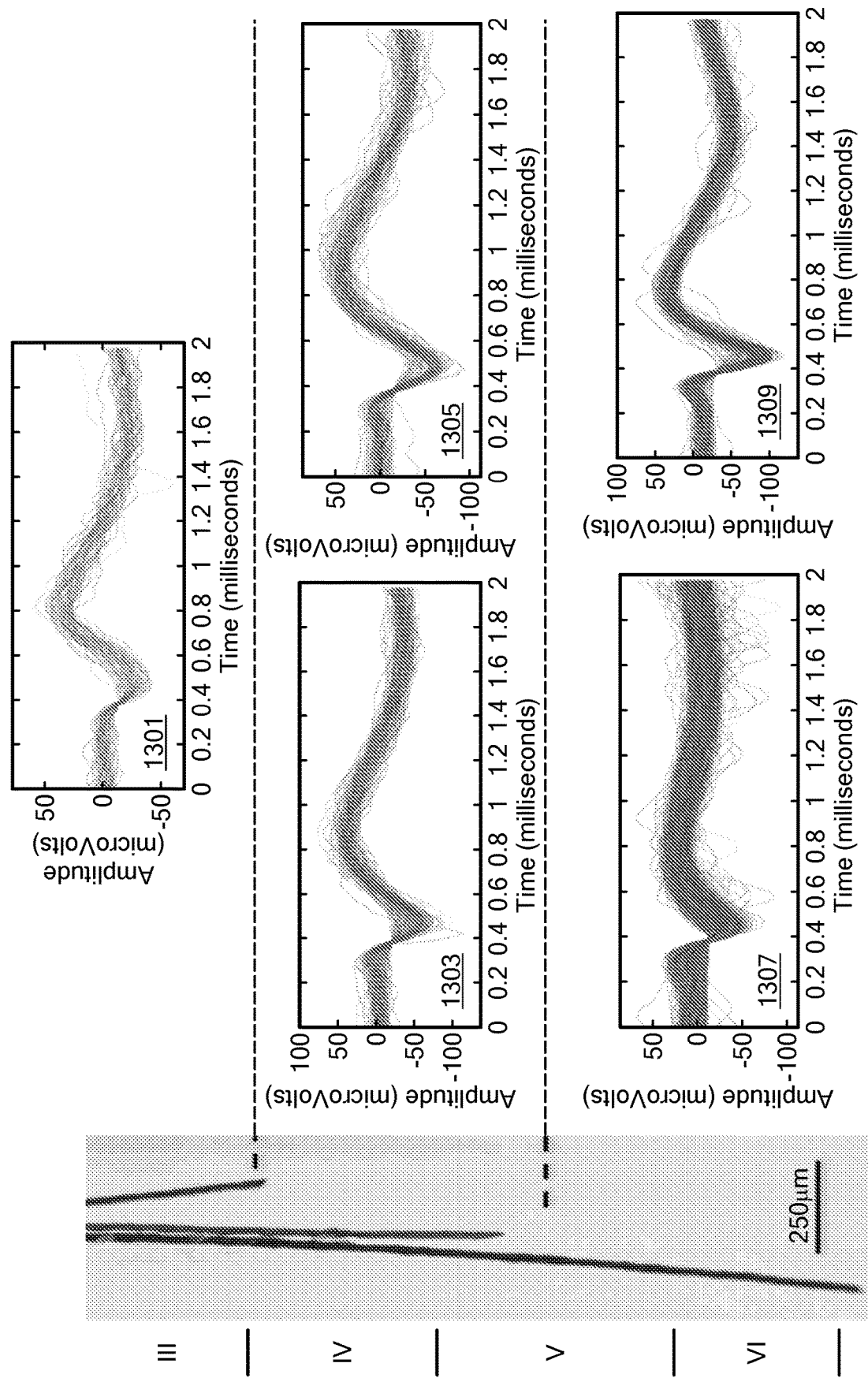
FIG. 13 provides neural activity recorded by a metallized graphene fiber electrode built in accordance with some embodiments of the present disclosure.

FIG. 13 illustrates in-vivo Cortical Neural Recording using four array electrodes. As illustrated, electrodes may be inserted into layers 3-6 of the brain. Four waveforms, one for each electrode, may be recorded 1303, 1305, 1307, and 1309. A composite waveform 1301 may be determined.

Figure 14:
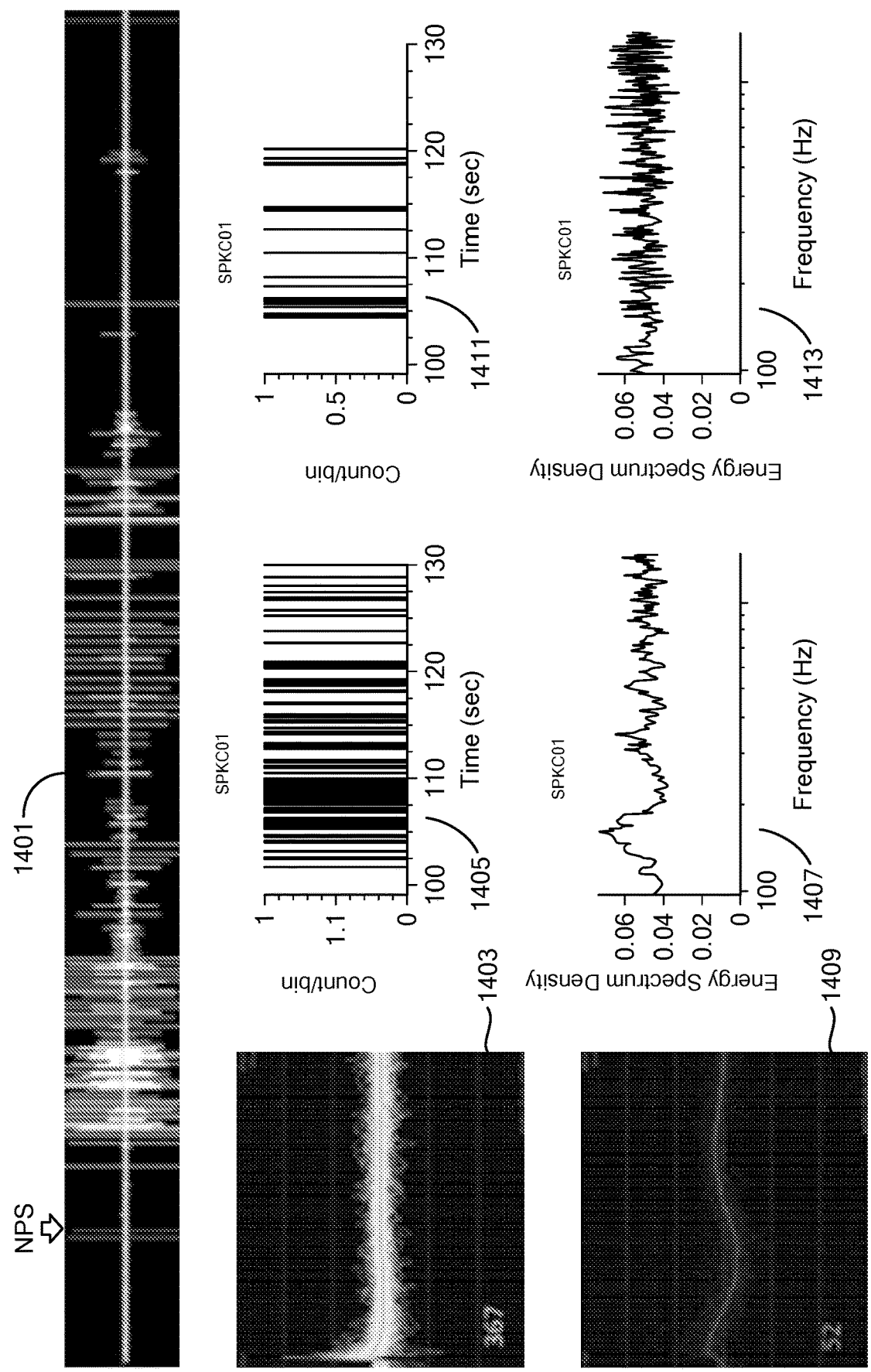
FIG. 14 provides neural activity recorded by a metallized graphene fiber electrode built in accordance with some embodiments of the present disclosure.

FIG. 14 illustrates a recording of endogenous activity from the splenic nerve evoked by the administration of nitroprusside (NPS), a molecule that reduces blood pressure. As illustrated, the graphene fiber electrode, made in accordance with the disclosure described herein, is able to record spontaneous neural activity from one of the terminal branches of the splenic nerve. As illustrated in the panel 1401, the test involves the recording of baseline activity for 2 min. After that an intravenous injection of nitroprusside (NPS) a vasodilator drug that reduces the blood pressure is administered (green arrow shows the time of injection). Approximately 1 min after the injection, a high amplitude neural activity is recorded from the graphene electrode (white vertical traces). Off-line analysis shows two specific waveforms in that evoked activity. One waveform is illustrated at 1403 that appeared 367 times after the NPS, with high incidence prior to 1000 seconds and relatively low frequencies, and the other waveform illustrated in 1409 observed 52 times that appeared at lower frequencies. Also illustrated is the power spectrum signal 14-7 and 1413, and frequency 1405 and 1411, respectively. FIG. 14 demonstrates the ability to record physiological relevant neural signals in the spleen using the graphene fiber electrode wrapped around this small (60-80 micrometer) size nerve.

Figure 15:
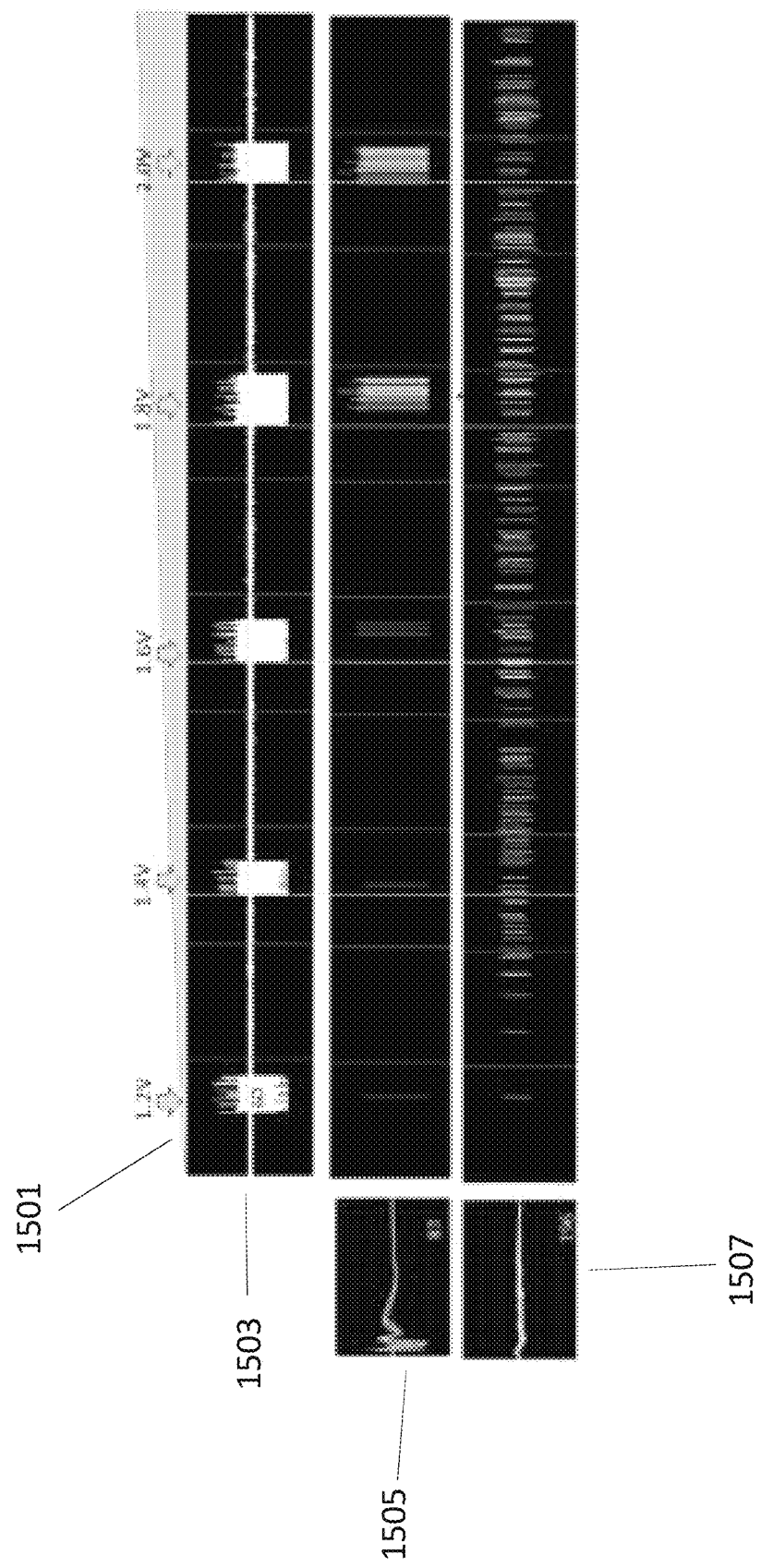
FIG. 15 provides neural activity recorded by a metallized graphene fiber electrode built in accordance with some embodiments of the present disclosure.

FIG. 15 illustrates the recording of nerve activity, evoked with a hook electrode at increasing voltage, using the graphene fiber electrode. In particular the recording is of compound action potentials from the splenic nerve evoked by electrical stimulation at increasing voltages (1.2, 1.4, 1.6, 1.8 and 2 V) 1501 applied to the vagus nerve using a commercial hook electrode (arrows). Two distinct waveforms were identified in the splenic nerve using the graphene fiber electrodes, one shown in the top panel 1505 and the other in the bottom panel 1507; that appeared at increasing numbers in response to the higher voltage stimulations 1503. This data confirms the ability of the graphene fiber electrodes built in accordance with the present disclosure to record neural signals in small nerves.

Figure 16:
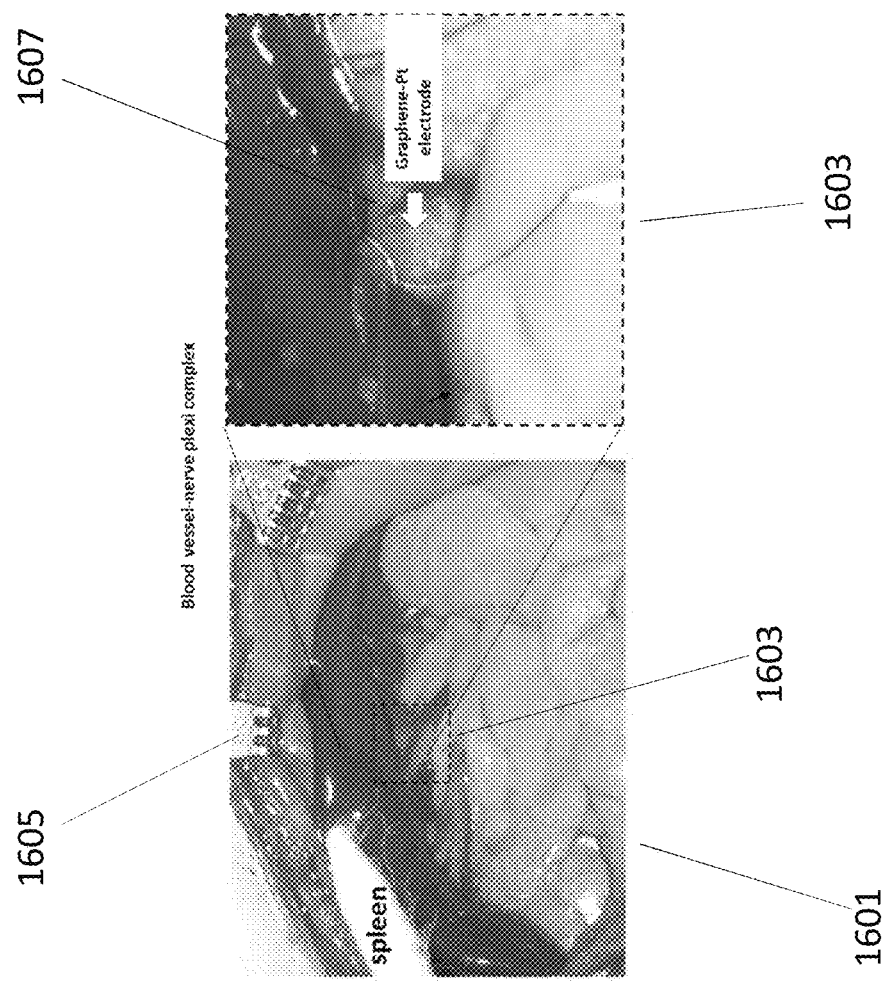
FIG. 16 provides implantation characteristics for a metallized graphene fiber electrode built in accordance with some embodiments of the present disclosure.

FIG. 16 illustrates engagement of a graphene-Pt electrode to a small terminal branch of the splenic nerve by tying over the Graphene-Pt fiber electrode to splenic plexi to record or stimulate nerve activity. 1601 is a photograph of a rat spleen slightly lifted 1605 to visualize the small terminal branches (insert 1603). A higher magnification of the branch is shown in the right 1603, where a blood vessel is seen with some fat cells at the bottom. It is known that a mesh (i.e., plexi) of nerves wrap the blood vessel and brings neural control to the spleen. The photograph in FIG. 16 also shows a graphene fiber electrode 1607 (made in accordance with the present disclosure described herein) that is wrapped around the blood vessel/plexi to record neural activity.

Figure 17:
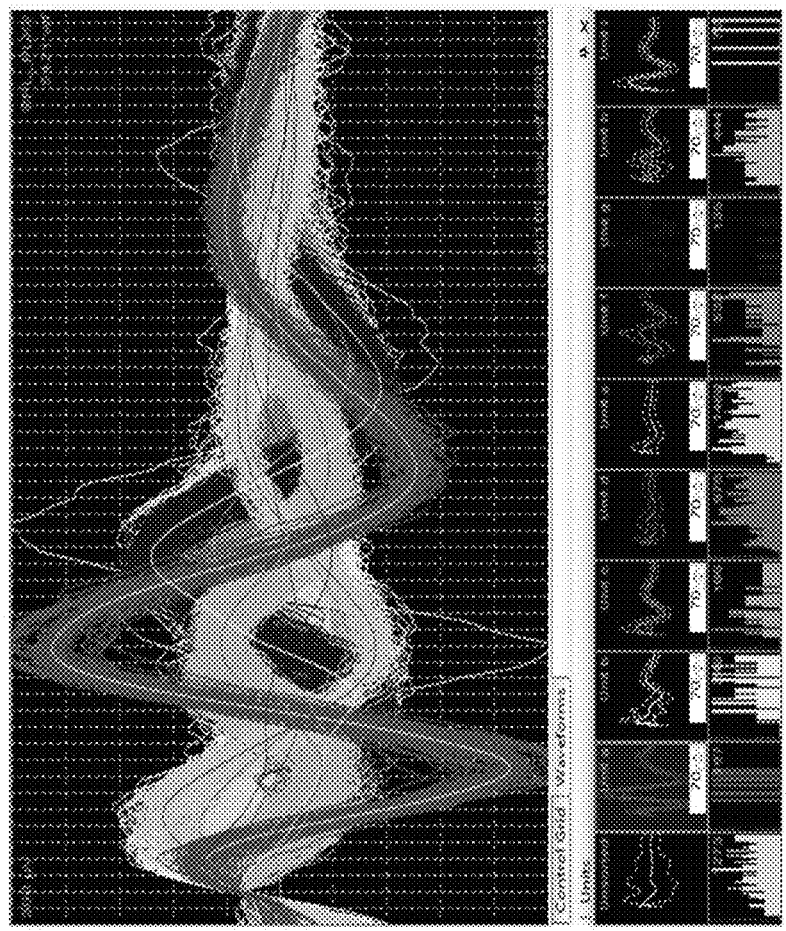
FIG. 17 provides neural activity recorded by a metallized graphene fiber electrode built in accordance with some embodiments of the present disclosure.

FIG. 17 illustrates different waveforms that represent various types of neural activity recorded from the terminal splenic plexi using a Graphene-Pt electrode per the present disclosure. Nine different waveforms recorded with the graphene fiber electrode are illustrated.

Figure 18:
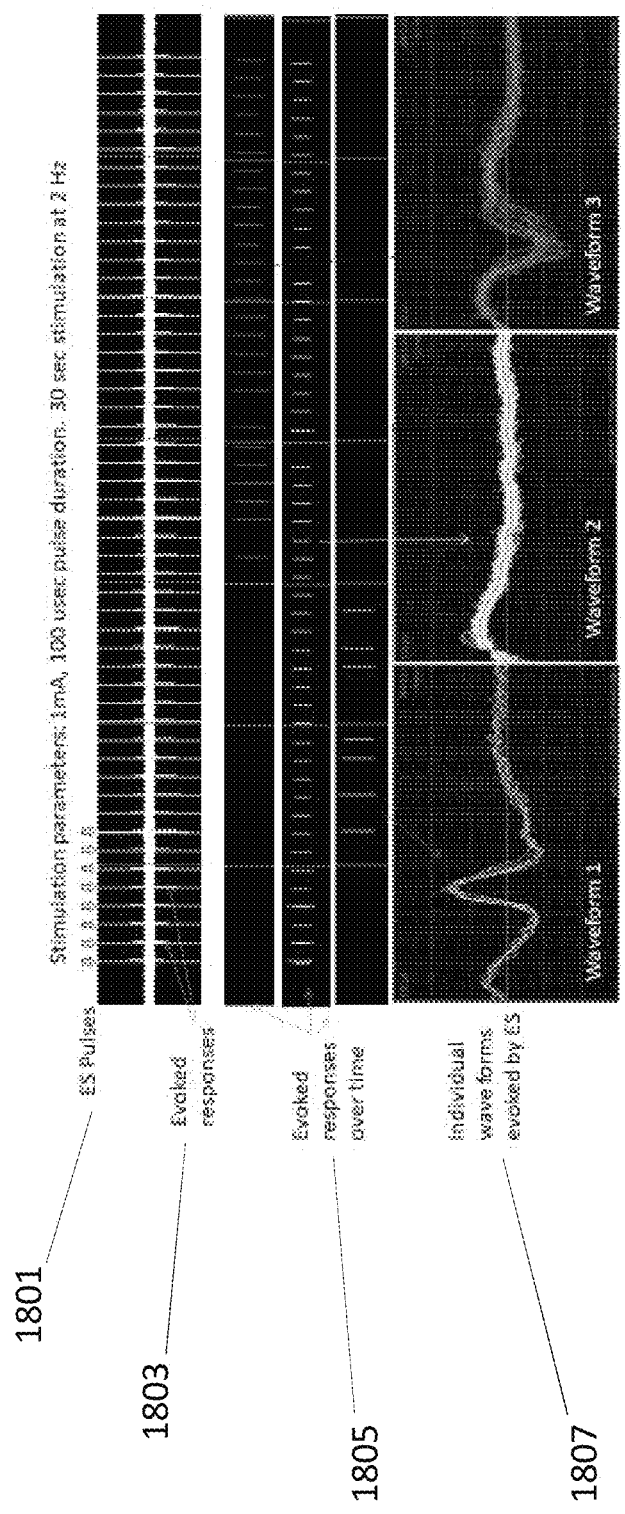
FIG. 18 provides neural activity recorded by a metallized graphene fiber electrode built in accordance with some embodiments of the present disclosure.

FIG. 18 illustrates the electrical stimulation capabilities for graphene fiber electrodes as made per the description herein. Two graphene fiber electrodes were inserted into the sciatic nerve in the rat, one serve as cathode and the other as anode. A train of electrical pulses were applied through the graphene fiber electrodes and the evoked activity recorded from a more proximal segment using a hook electrode. The figure shows that with increased electrical pulses 1801 (yellow arrows) we were able to recruit three different types of neural signals, each from different neuronal populations, shown in 1803, 1805, corresponding to three different waveforms 1807. This data confirms that the graphene fiber electrodes of the present disclosure are able to evoke specific neural activity through electrical stimulation.

Example 2

Electrode Fabrication

In accordance with the techniques described herein graphene fiber electrodes with a 20 micrometer diameter, graphene fiber electrodes coated with platinum with a 20 micrometer diameter, graphene fiber electrodes with a 40 micrometer diameter, and graphene fiber electrodes coated with platinum and having a 40 micrometer diameter were fabricated.

Figure 19:
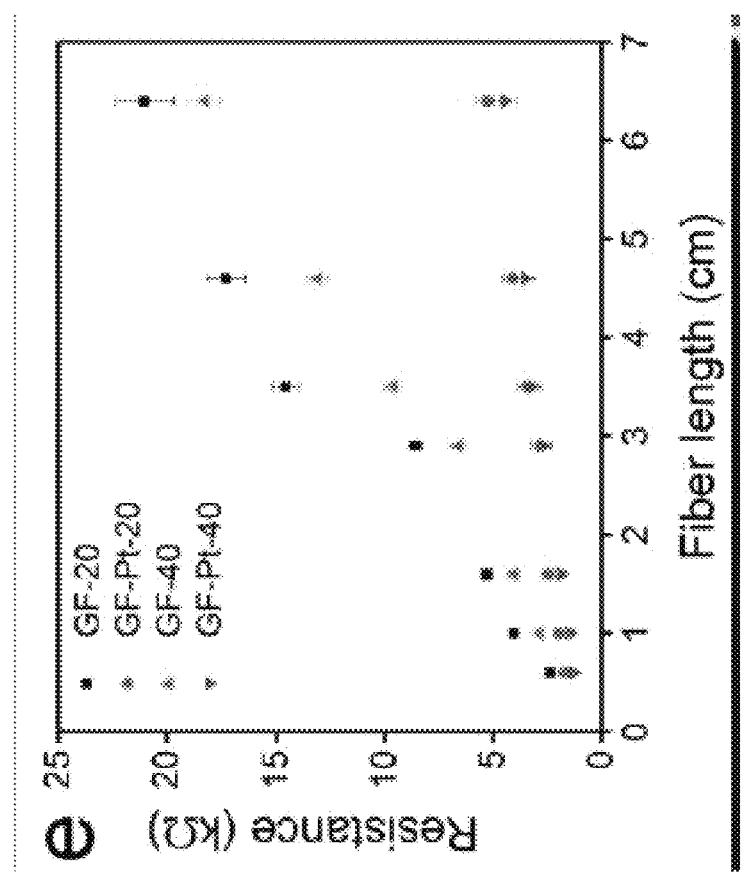
FIG. 19 provides a characterization of a metallized graphene fiber electrode built in accordance with some embodiments of the present disclosure.

FIG. 19 illustrates the resistance for the four types of graphene fiber electrodes at various fiber lengths. As illustrated the resistivity increases with increased fiber length.

Electrochemical Characterization

Figure 20:
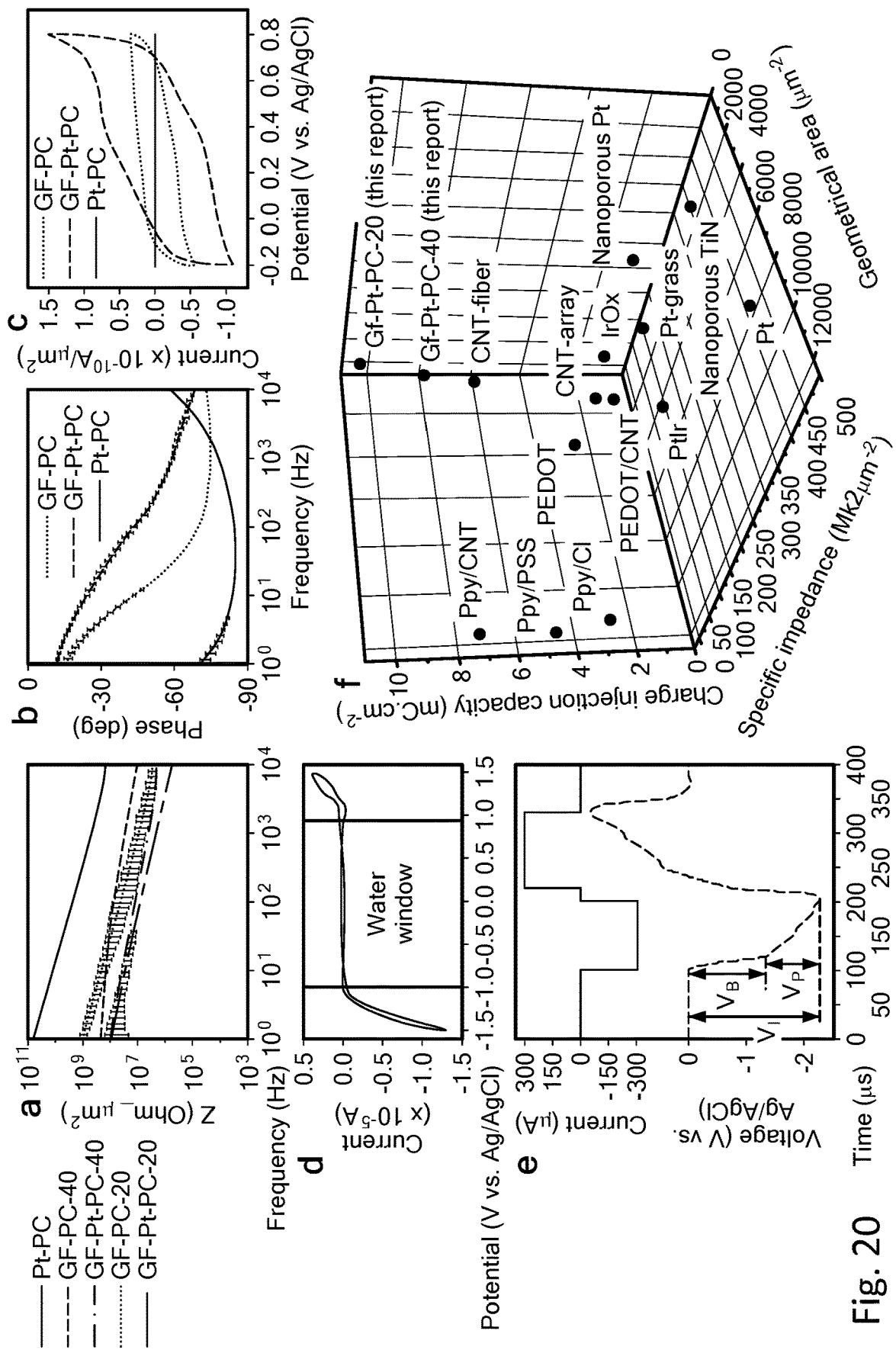
FIG. 20 provides a characterization of a metallized graphene fiber electrode built in accordance with some embodiments of the present disclosure.

FIG. 20 provides electrochemical characterization of various microelectrodes made from Pt, graphene microfibers, and Pt coated graphene microfibers (D=20 and 40 µm). Panel A of FIG. 20 provides modulus impedance of microelectrodes. Panel B of FIG. 20 provides phase angle of impedance of microelectrodes. Panel C of FIG. 20 provides CVs of the microelectrodes at 10 mV s$^{-1}$ in PBS solution. Panel D of FIG. 20 provides water window of the microelectrodes. Panel E of FIG. 20 provides voltage transient test of microelectrodes. Panel F of FIG. 20 provides a comparison of the charge injection capacity, specific impedance at 1 kHz, and geometrical area of the modified microelectrodes with conventional neural interfacing electrodes.

Electrochemical characterizations were performed in accordance with the techniques discussed above in relation to Example 1.

Durability Characterization

Figure 21:
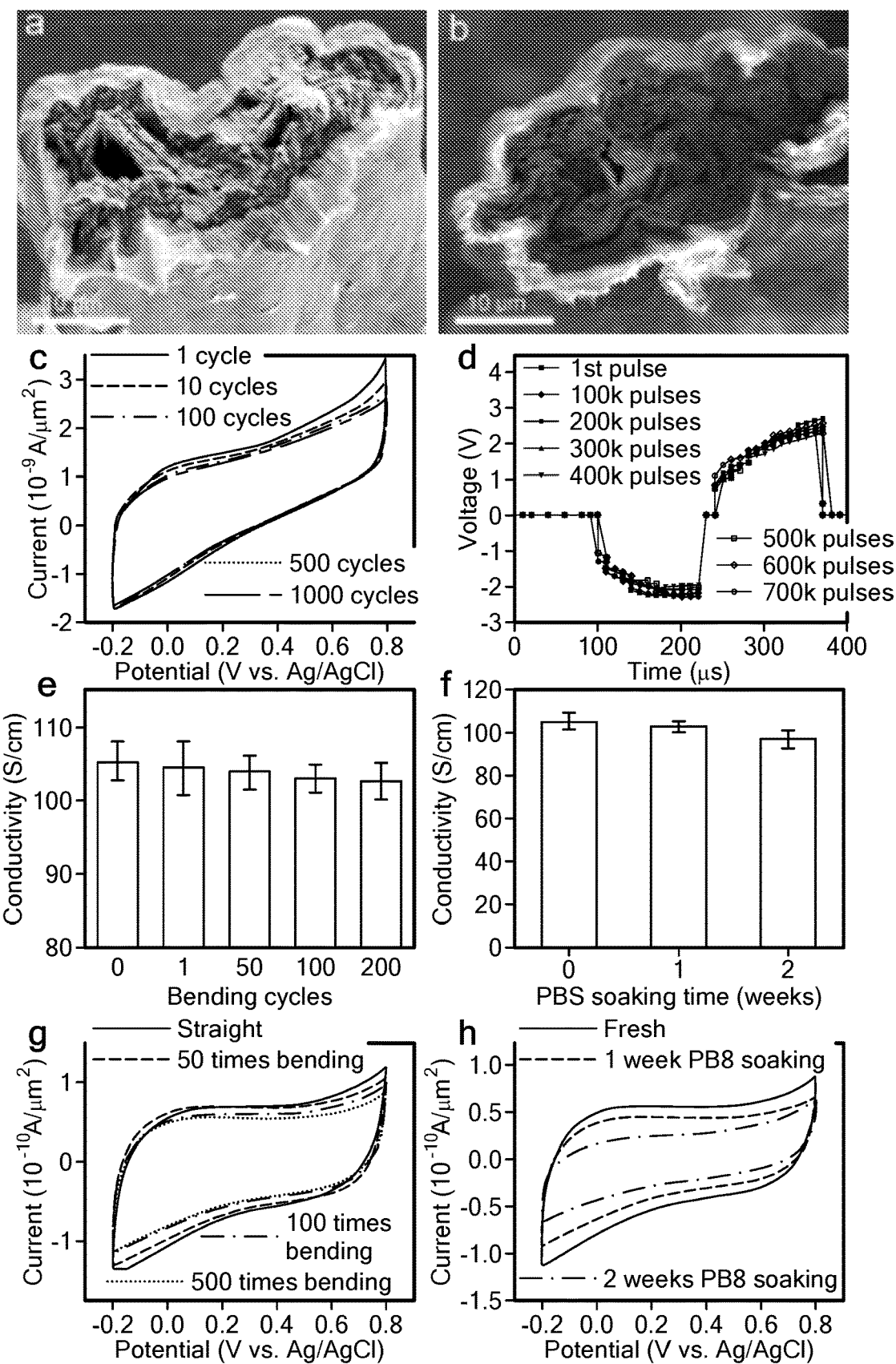
FIG. 21 provides a characterization of a metallized graphene fiber electrode built in accordance with some embodiments of the present disclosure.

FIG. 21 illustrates the electrochemical durability characterization of the modified microelectrodes (GF-Pt-PC-40). In particular, Panels A and B of FIG. 21 illustrate cross-section SEM images of a typical modified microelectrode before (Panel A) and after (Panel B) 1000 CV cycles at scan rate of 50 mV s$^{-1}$, showing high stability of the microelectrodes. Panel C of FIG. 21 shows prolonged CV of the modified microelectrodes, 1000 cycles at scan rate of 50 mV s$^{-1}$. Panel D of FIG. 21 shows prolonged pulse stability of the modified microelectrodes. Panel E of FIG. 21 shows electrical conductivity of the modified graphene microfibers after successive bending cycles, 0 refers to the straight fiber, while 1 refers to the fiber that was 360° bent. Panel F of FIG. 21 shows electrical conductivity of the modified graphene microfibers after prolonged PBS soaking. Panels G and H of FIG. 21 show the CV of the modified microelectrodes after successive bending and prolonged PBS soaking, respectively. Number of repeats is four independent tests.

Durability characterizations were performed in accordance with the techniques discussed above in relation to Example 1.

Example 3

Single Unit Recordings of Central and Peripheral Nervous System Neurons Using Graphene Electrodes Interfacing the nervous system to decode functional activity or to electrically stimulate to modulate this function, has a number of scientific and medical applications applications. Materials used in the design of neural interfaces are desired to have low impedance with high signal-to-noise ratio (SNR) to allow for sensitive recording of single unit activity, and high charge storage capacity (CSC) for effectively and safe neural stimulation. Microelectrodes are commonly fabricated in silicon with platinum (Pt), Pt/Iridium and Iridium oxide electrodes. However, the micromotion of the silicone shafts implanted into the soft nervous tissue exacerbates the foreign body response and contributes to the eventual failure of these devices. The alternative use of carbon nanotube coated microelectrodes has been promising due to their biocompatibility and high CSC (~372 mC/cm$^2$) and low impedance (~20 MΩ), however the stiffness of the metal shafts and delamination of the carbon nanotube coating limits the chronic use of these electrodes. The production of graphene fibers from liquid crystalline dispersions of graphene oxide (LCGO) demonstrated excellent electrochemical and mechanical characteristics. Electrodes built in accordance with the present disclosure are used to record brain and peripheral nerve activity. Single fibers and multi-electrode arrays were implanted in the motor cortex and sciatic nerve of adult rats (n=5). The electrodes effectively recorded single neuronal units, with excellent SNR. Together, the data supports the use of graphene fibers as intraneural electrodes for the neural interfacing of brain and peripheral nerve activity.

Electrode Fabrication

Figure 22:
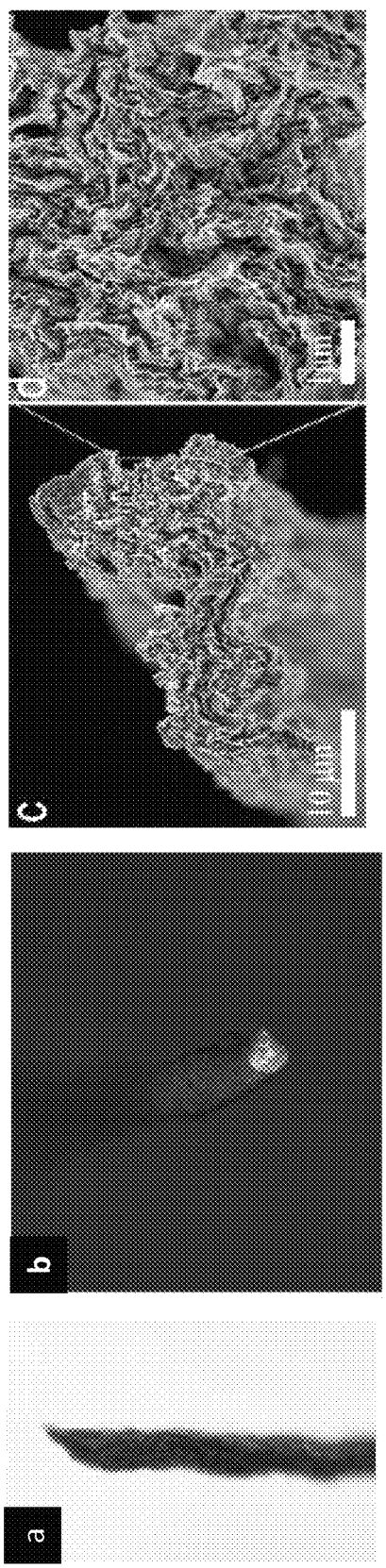
FIG. 22 provides a characterization of a metallized graphene fiber electrode built in accordance with some embodiments of the present disclosure.

FIG. 22 illustrates graphene electrodes built in accordance with the present disclosure. Panels A and B illustrate 20-40 micrometer graphene fibers obtained by the extrusion of LCGO in an acidic coagulation bath, which were subsequently coated with Parylene C. Panels C and D illustrate scanning electron microscopy images of the graphene fibers.

Surgical (In-Vivo) Implantation and Neural Activity Recording

Figure 23:
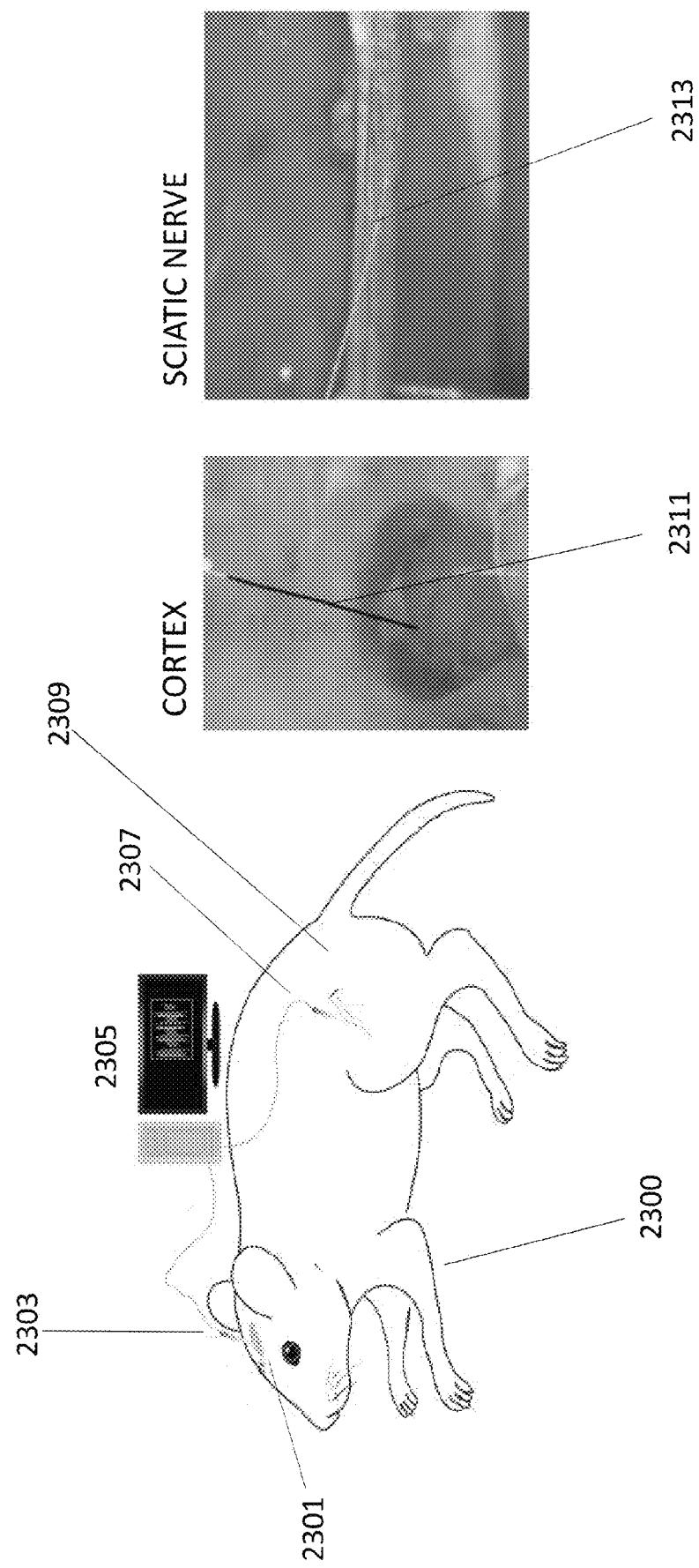
FIG. 23 provides implantation characteristics for a metallized graphene fiber electrode built in accordance with some embodiments of the present disclosure.

As illustrated in FIG. 23, graphene electrodes were implanted into the motor cortex or sciatic nerve of adult female rats 2300. In particular, metallized graphene electrode multi-array 2303 was implanted in the motor cortex 2301. Additionally, a single metallized graphene electrode 2307 was implanted in the sciatic nerve 2309. Signals from the graphene electrodes were transmitted to a recording system 2305.

Figure 24:
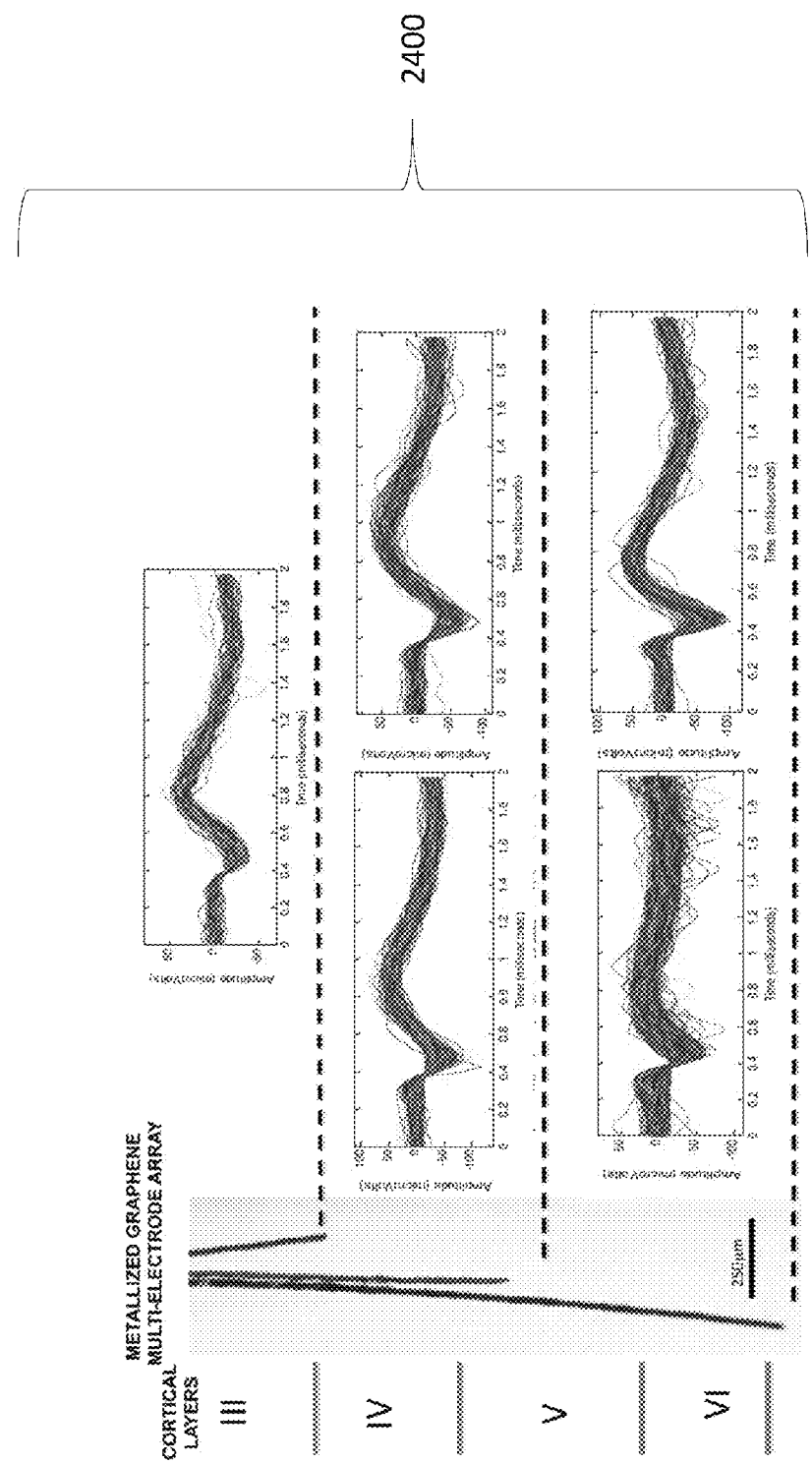
FIG. 24 provides neural activity recorded by a metallized graphene fiber electrode built in accordance with some embodiments of the present disclosure.

As illustrated in FIG. 24, single unit recordings 2400 were recorded from the motor cortex. Multi-electrodes were implanted in different depths of the motor cortex and as such single unit recordings were obtained from different cortical layers.

Figure 25:
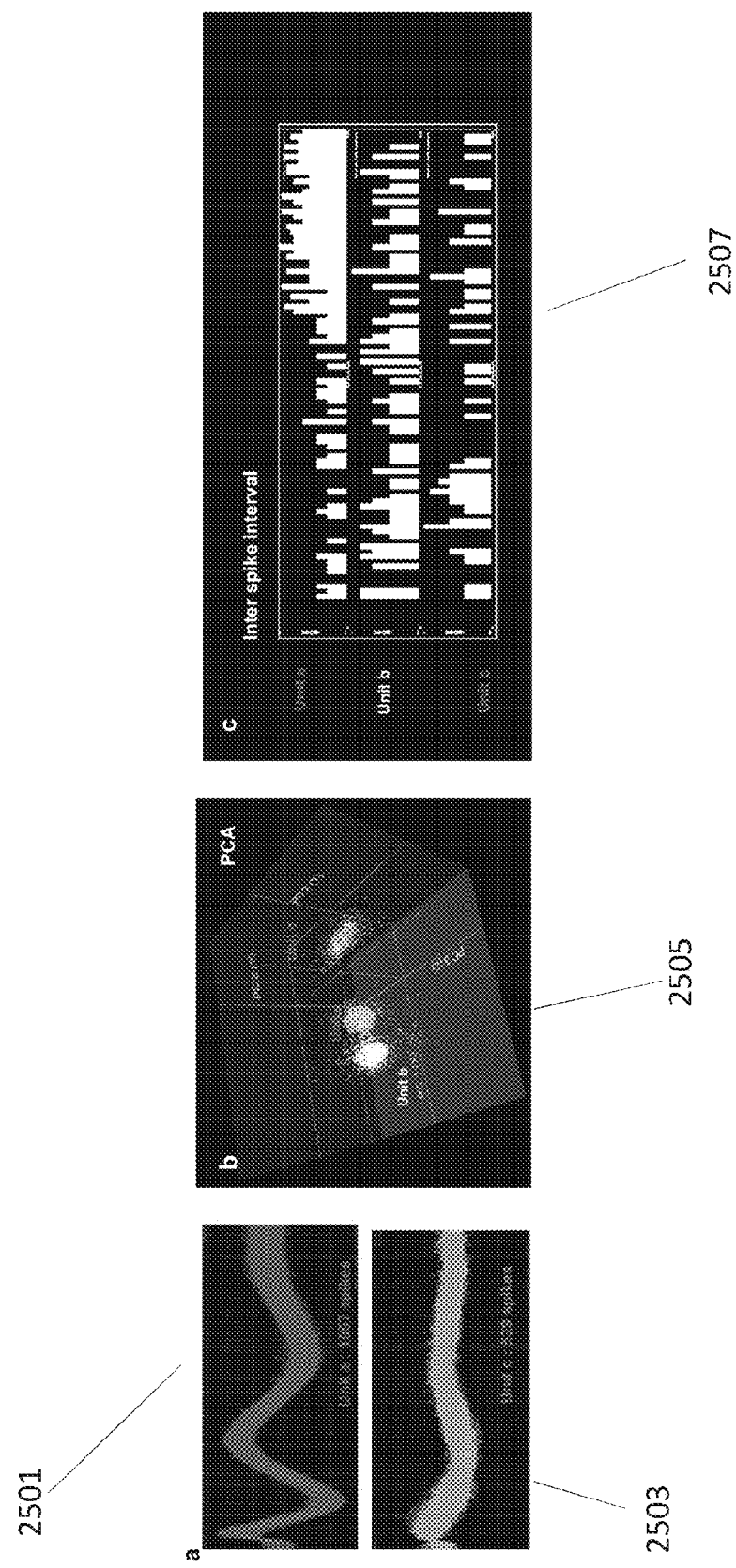
FIG. 25 provides neural activity recorded by a metallized graphene fiber electrode built in accordance with some embodiments of the present disclosure.

As illustrated in FIG. 25, recordings from the motor cortex and sciatic nerve were plotted using a raster plot 2501, 2503 and illustrated the activity of three independent axons (as shown in the PCA plot of Panel B of FIG. 25). Further, the inter spike interval 2507 was plotted.

FIGS. 22-25 illustrate that graphene micro-electrodes may be used as high performance interfaces for central and peripheral nervous system. Further, the application of a metallic coating on the graphene fibers conveys excellent electrochemical characteristics to the material. Additionally, the design of multi electrode arrays of graphene fibers represents an alternative for recording multiple single neuronal units a high sensitive performance.

Example 4

Intra and Extraneural Activity in the Vagus Nerve Recorded by Platinized Graphene Fiber Electrodes Interfacing the vagus nerve (VN) allows researchers to decode and modulate its activity. FDA approved clinical therapies based on VN stimulation include drug resistant epilepsy and depression, and the vagus nerve is currently being investigated for morbid obesity, tinnitus and stroke. The VN has a heterogeneous anatomical composition (~80% afferents and ~20% efferent fibers) resulting in complex functional electrophysiology that responds in a unique way to different physiological stimulus. Conventional electrodes to interface the VN are fabricated with platinum or platinum iridium and have limited sensitivity and low charge injection capacity (Qinj, ~0.05-0.26 mC/cm2), whereas intraneural electrodes fabricated with carbon nanotubes have shown promise (CSC ~372 mC/cm2, 12.5 kΩ).

In Example 4, high performance platinized graphene fibers obtained from liquid crystalline dispersions of graphene oxide, with excellent electrochemical characteristics (CSC and Qinj ~947 and ~46 mC/cm2 respectively) are implanted in the VN and in order to use them to record evoked electrophysiological activity in both, extraneural and intraneural configurations during: i) systemic reduction in Oxygen tension, ii) decreased mean arterial pressure induced by intravenous nitroprusside treatment, and iii) evoked activity in response to proximal VN stimulation using a platinum hook electrode. Specific activity waveforms and activity patterns were correlated to the treatments over baseline conditions with high signal to noise ratios (SNR-4.3). The data supports the use of platinized graphene fibers as extraneural and intraneural electrodes for interfacing the VN.

Electrode Fabrication

Figure 26:
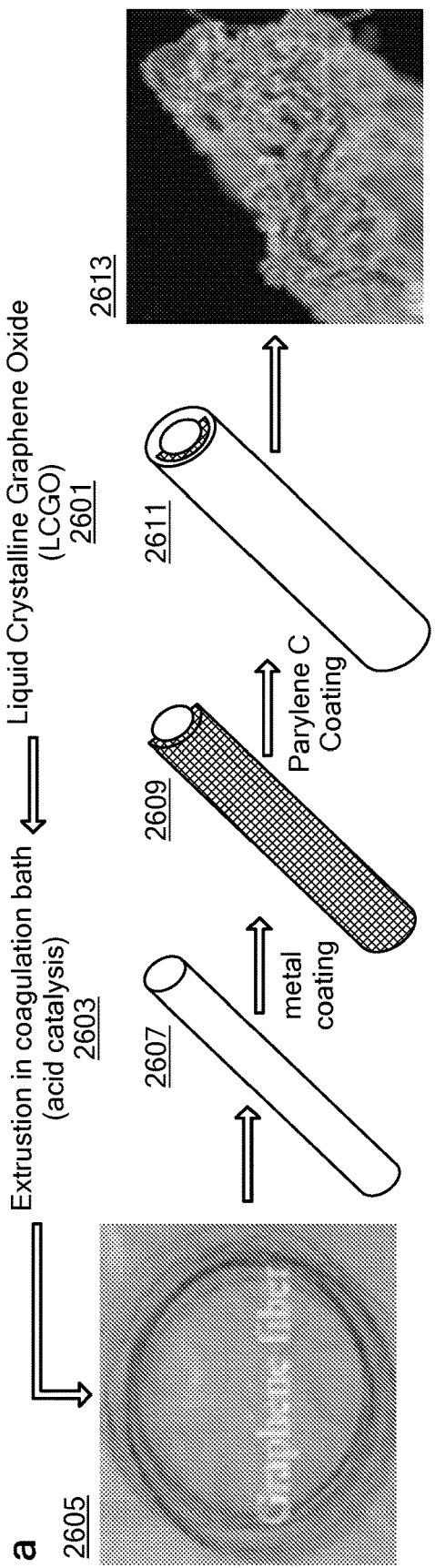
FIG. 26 provides a characterization of a metallized graphene fiber electrode built in accordance with some embodiments of the present disclosure.
Figure 26:
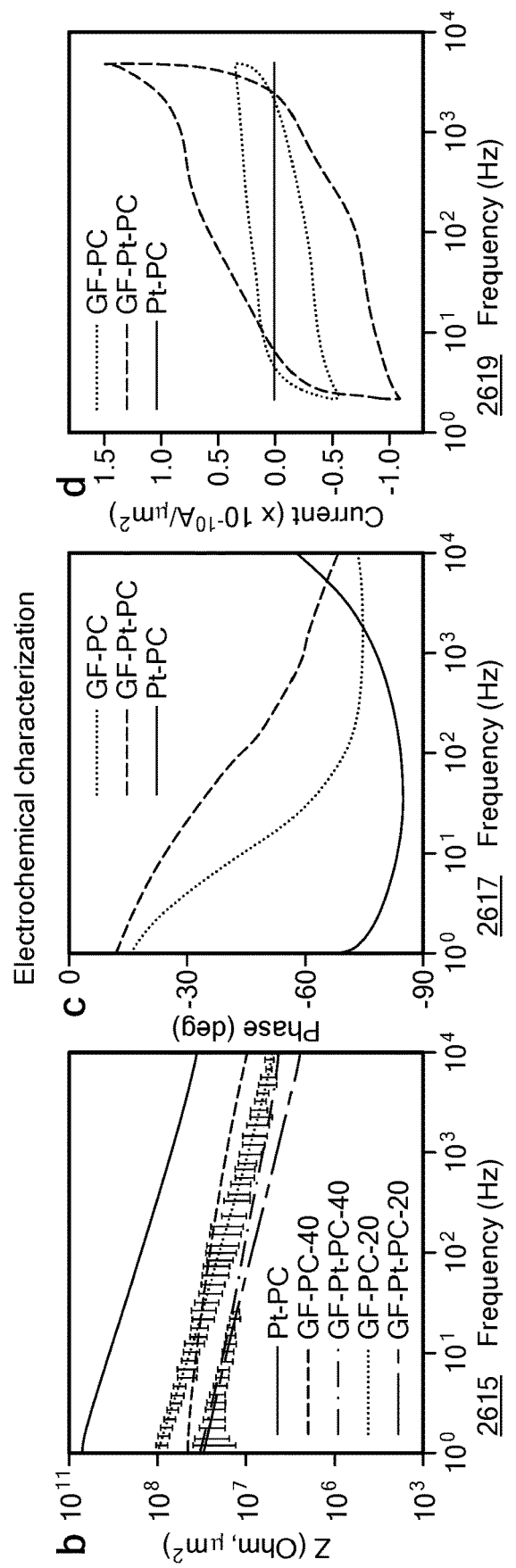

Panel A of FIG. 26 illustrates the electrode fabrication steps. In particular, using LCGO 2601 followed by an extrusion in a coagulation bath 2603, graphene fibers 2605 are developed, cut 2607, coated with metal (i.e., platinum) 2609, coated with an insulating material (i.e., Parylene-C) to form a GF-Pt microelectrode 2611. A SEM image of the microelectrode is provided 2613.

Electrochemical Characterization

Panels B, C, and D of FIG. 26 illustrate the impedance spectroscopy 2615, phase angle 2617 and cyclic voltammetry of graphene fibers coated with PC (GF-Pt-PC) at 20 and 40 μm OD, compared to Pt-PC wires 2619.

Surgical (In-Vivo) Implantation and Neural Activity Recording

Figure 27:
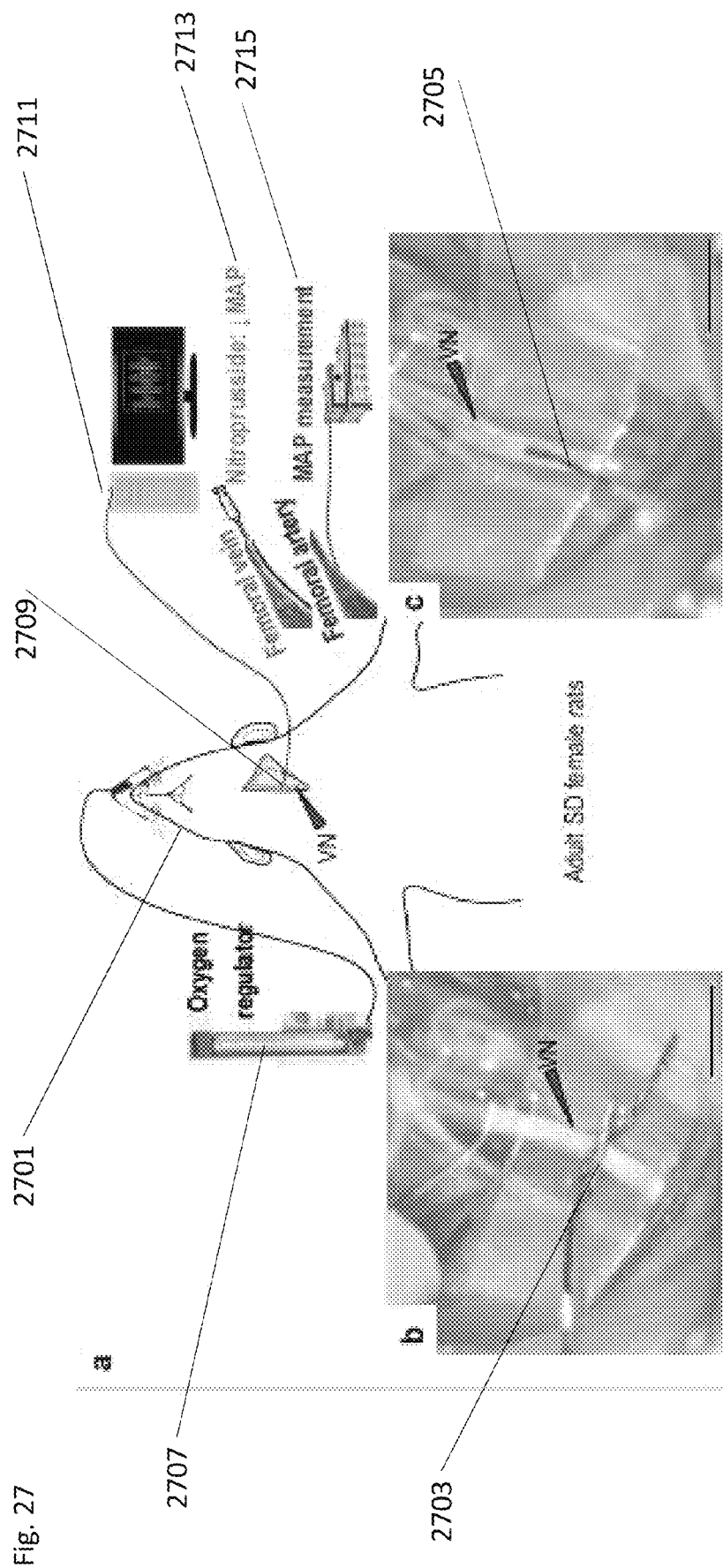
FIG. 27 provides implantation characteristics for a metallized graphene fiber electrode built in accordance with some embodiments of the present disclosure.

FIG. 27 illustrates a surgical implantation of electrodes built in accordance with embodiments of the present disclosure. In particular, as illustrated, electrodes are implanted into an adult female rat 2701. The graphene electrodes were either implanted extraneurally 2703 (see panel B of FIG. 27) or intraneurally 2705 (see panel C in FIG. 27) in the cervical vagus nerve (VN) 2709. The rat 2701 was oxygenated during the surgery and neurostimulation/neurorecording procedure. Three techniques were used to evoke neural activity: vagus nerve stimulation (VNS), application of nitroprusside, and oxygen reduction. Electrical activity from the vagus nerve 2709 was recorded and provided to researchers 2711. Nitroprusside was administered 2713 via the femoral vein of the rat 2701. Oxygenation measurements and/or blood pressure measurements were recorded 2715 at the femoral artery.

Figure 28:
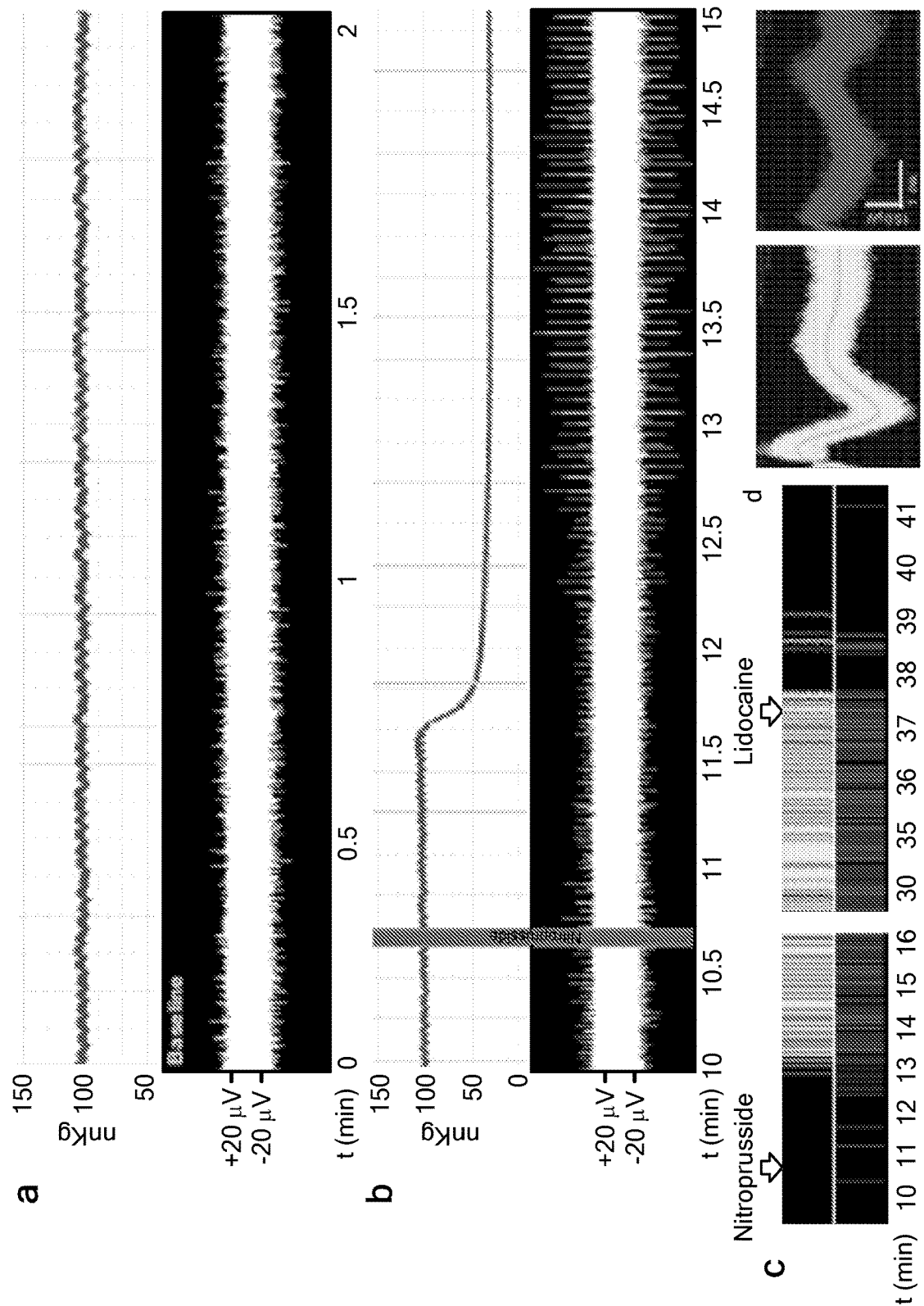
FIG. 28 provides neural activity recorded by a metallized graphene fiber electrode built in accordance with some embodiments of the present disclosure.

FIG. 28 provides a summary of the results of the in vivo testing setup described in FIG. 27 and more particularly, vagus nerve activity evoked by hypotension due to systemic nitroprusside. In particular, panel A illustrates baseline blood pressure measurements from the femoral artery and recordings of neural activity from graphene electrodes implanted in the vagus nerve. Panel B of FIG. 28 illustrates blood pressure measurements and recordings of neural activity from graphene electrodes implanted in the vagus nerve as evoked by induced hypotension. Panel C illustrates the neural activity response to administration of nitroprusside and lidocaine in a raster plot. As illustrated in Panel D, two separate wave forms were identified.

Figure 29:
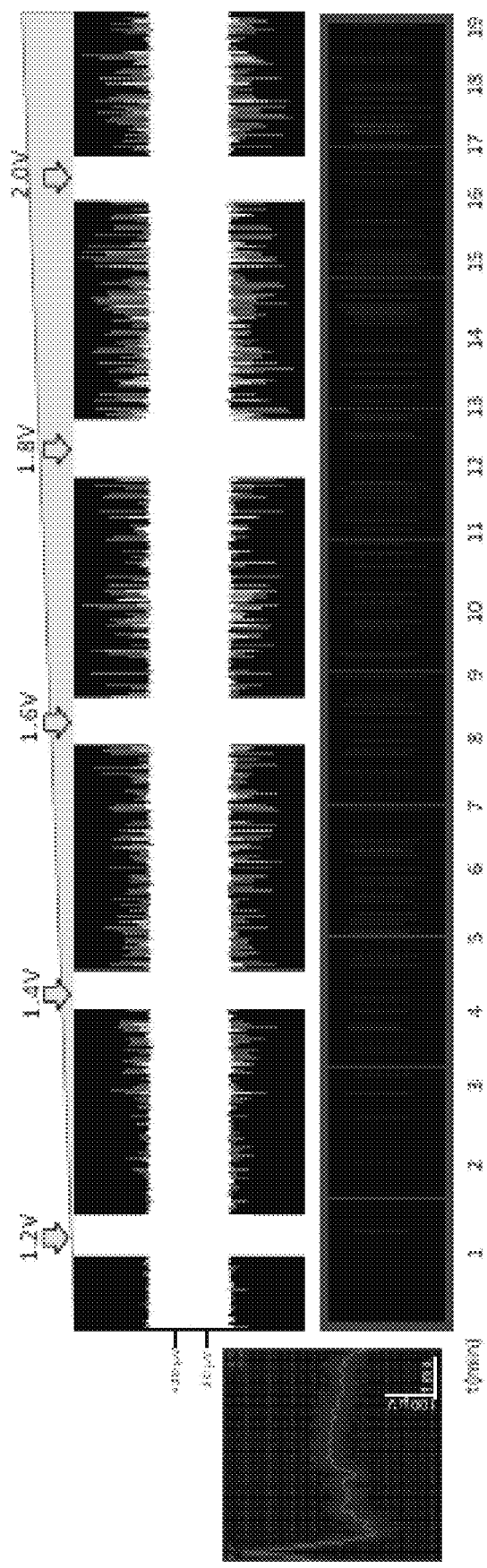
FIG. 29 provides neural activity recorded by a metallized graphene fiber electrode built in accordance with some embodiments of the present disclosure.

FIG. 29 illustrates evoked activity by electrical stimulation. As shown in the top plots of FIG. 29, the frequency and amplitude of compound action potentials increased as a function of intensity. As illustrated in the bottom panel, one wave form and its corresponding raster plot was identified.

Figure 30:
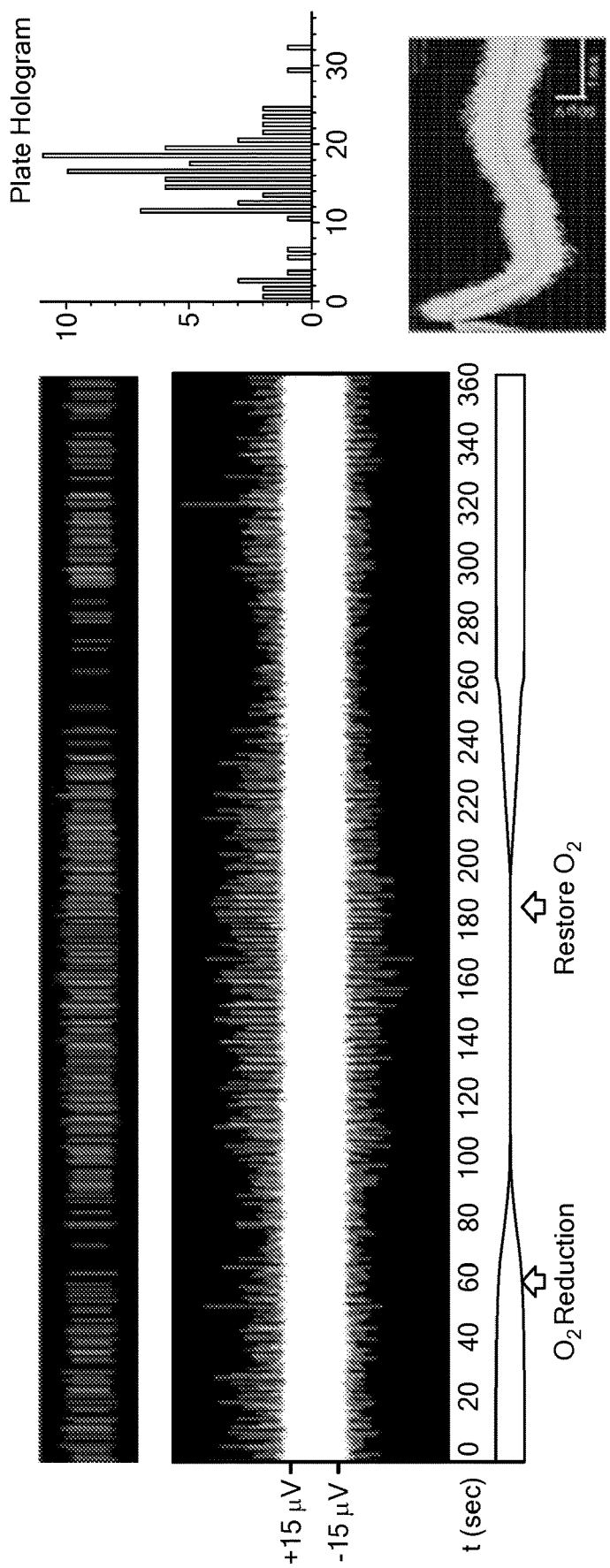
FIG. 30 provides neural activity recorded by a metallized graphene fiber electrode built in accordance with some embodiments of the present disclosure.

FIG. 30 illustrates neural activity detected by intraneural graphene fibers implanted in the cervical VN in accordance with the disclosure herein. Oxygen restriction increased the amplitude of neural electrical activity. A corresponding increase in frequency was noted in the raster plot of the selected wave form (bottom right panel of FIG. 30), which is represented in the rate histogram (top right panel of FIG. 30). The bottom trace provides a schematic indication time of Oxygen reduction from 2 to 0 L/min.

Example 4 as illustrated by FIGS. 26-30, demonstrates that platinized graphene fiber electrodes may be used as a high performance neural interface, to record neuronal activity in the cervical VN, both extra- or intraneurally. The electrochemical properties of these electrodes (low resistance and high conductivity) allowed to effectively identify single and compound nerve units with a SNR-4.3. The effective detection of electrical activity evoked by electrical stimulation, decrease in blood pressure and during oxygen reduction support the use of these electrodes as autonomic neural interfaces to decode nerve electrical activity pertinent to bioelectronic medicine.

Example 5

Figure 31:
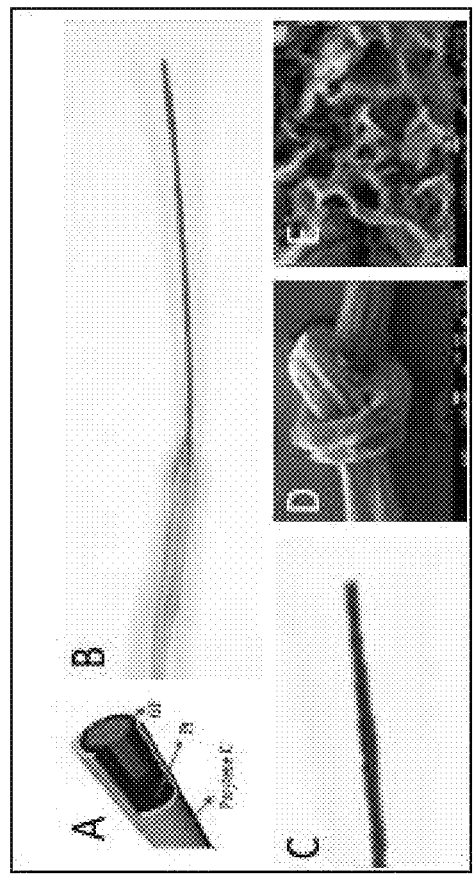
FIG. 31 provides a characterization of a metallized graphene fiber electrode built in accordance with some embodiments of the present disclosure.

Methods and Bioelectronic Applications of Platinized Graphene Fibers to Peripheral Nerves Electrode Fabrication As illustrated in Panel A of FIG. 31, graphene fiber microelectrodes coated with a ~200 nm layer Pt and insulated with 2 µm layer of Parylene-C (GF-Pt-PC) were fabricated in accordance with the system and methods described herein. The graphene fiber microelectrodes were connected to a silver wire as illustrated in Panel B of FIG. 31 and Panel C of FIG. 31. SEM imagery of the graphene fiber microelectrodes is presented in Panels D and E of FIG. 31, illustrating greater flexibility than conventional microelectrodes. Electrodes built in accordance with the present disclosure can be used as an array of different fibers, as a yarn, or strand multi-electrode arrays.

Electrochemical Characterization

Figure 32:
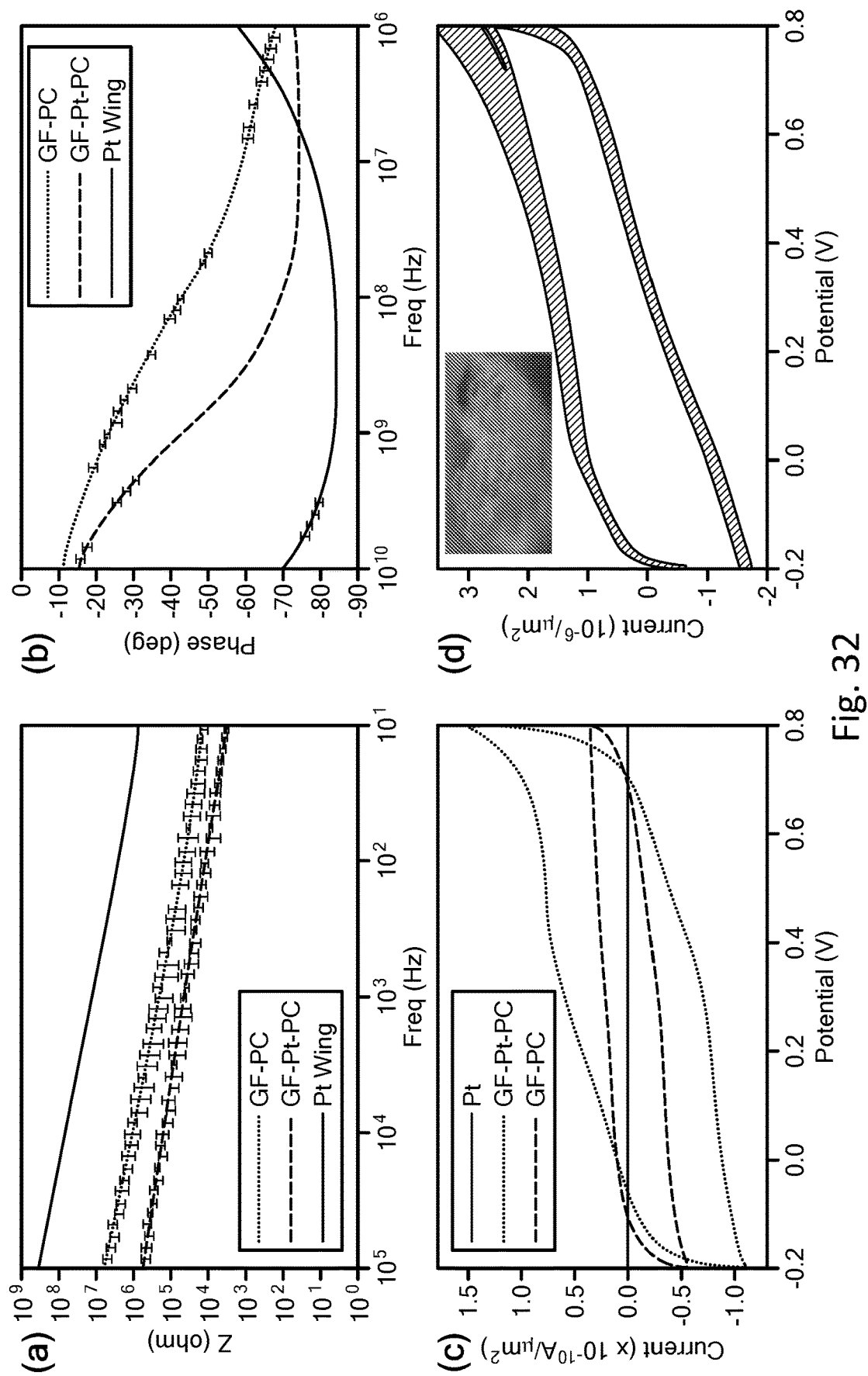
FIG. 32 provides a characterization of a metallized graphene fiber electrode built in accordance with some embodiments of the present disclosure.

As illustrated in FIG. 32, coating the graphene microfibers with a thin layer of Pt resulted in a strong synergistic effect leading to a robust and superior hybrid microelectrode with ~1 and ~3 orders of magnitude lower impedance than the original GF microfiber and Pt microelectrodes, respectively. The Pt coating increases significantly the conductivity to from 200 to 460 S/cm of a 40 µm GF fiber. Moreover, the cathodic charge storage capacity of the microelectrode, calculated from the CV, was 946 mC/cm$^2$, a value ~3 orders of magnitudes higher than Pt electrode and ~2 times higher than the original GF microfibers.

Surgical (In-Vivo) Implantation and Neural Activity Recording

Conventional peripheral nerve interfaces (PNIs) may be categorized based on their fabrication, sensitivity and invasiveness. Cuff electrodes are PNIs implanted circumferentially on the peripheral nerves, and made of flexible materials with helical, spiral, split-cylinder or folding designs to conform to their cylindrical shape, and metals contacts such as gold, platinum or platinum/iridium. Traditional cuff electrodes fabricated in silicone are commonly used due to their softness (i.e., Young's modulus in MPa range) and chronic stability, although their fabrication is mostly limited to molding and lamination techniques. Unfortunately, these conventional cuff devices have relative thick walls (e.g., 280-600 µm) needed to generate sufficient bending forces to keep them closed, which causes a significant foreign body response and epineurial fibrosis, negatively affecting the sensitivity of the interface. In addition, new clinical applications for the regulation of organ physiology involved in cardiac, respiratory, digestive and urinary conditions, focus on neuromodulation of autonomic peripheral nerves that are smaller and composed of fewer axons (i.e., approximately 600 axons averaging 2.5 µm in the 60-80 µm rat carotid sinus nerve). The nerve targets in these conditions also have a thinner epineurium, are formed mostly of unmyelinated axons and thus, likely more susceptible of damage by neurointerface devices. The small nerve size of these targets, their fragile nature, and restricted areas for implantation, are driving the development of new implantable electrodes that are small, flexible and with sufficient charge injection capacity for efficient and safe nerve stimulation.

Figure 33:
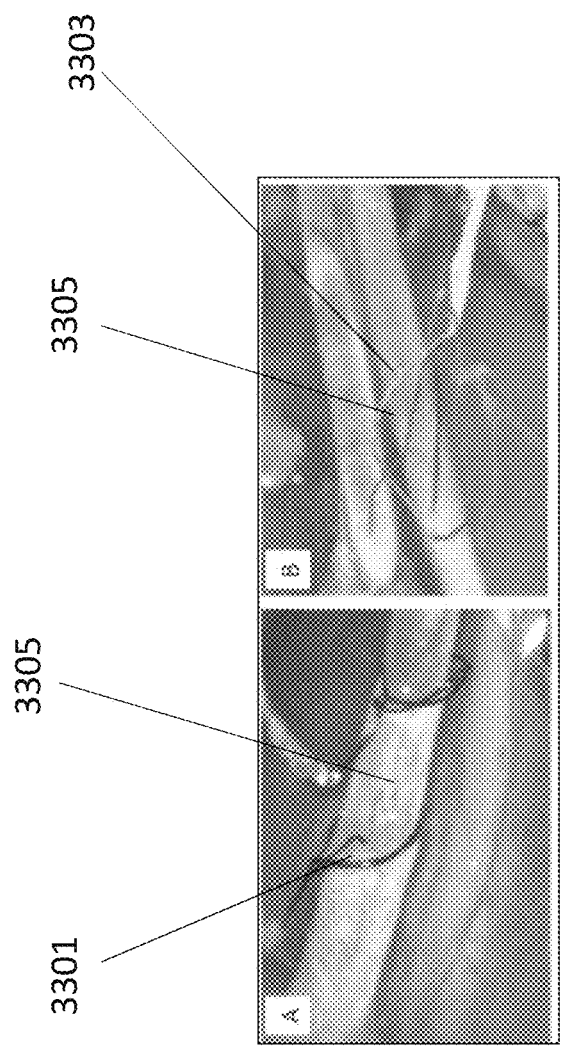
FIG. 33 provides implantation characteristics for a metallized graphene fiber electrode built in accordance with some embodiments of the present disclosure.

As illustrated in Panel A of FIG. 33, the disclosed GP-Pt fibers can be used as "cuffless" PNIs since they can be simply tied around 3301 the nerve 3305 and serve as a monopolar or multipolar electrodes for both recording and stimulation of nerves of any size, since the fiber can be used use to tie a knot and thus closes completely. This allows it to be placed in tightly over any nerve, nerve fascicle or nerve plexi and neuro-vascular plexi. The sensitivity of the electrodes is such that allows it to wrap it around small nerves sense their activity.

Alternatively, as illustrated in Panel B of FIG. 33, if the tips are sharpened, they can be used individually or as an array 3303, to record or stimulate intravascularly. When used as cuffless electrodes the segment around the nerve is deinsulated before placing it around the nerve.

Figure 34:
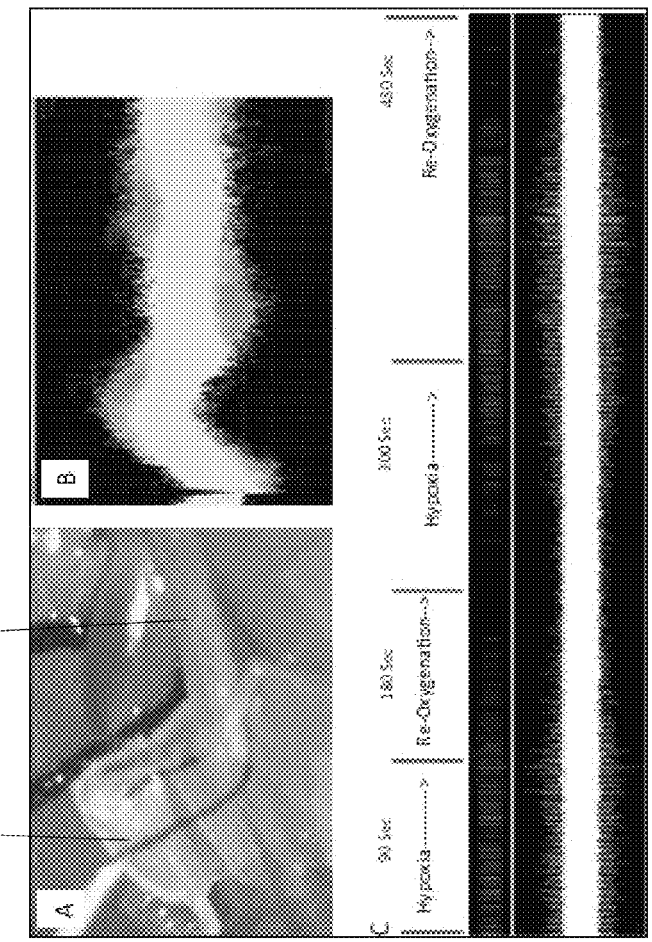
FIG. 34 provides implantation characteristics and neural recordings for a metallized graphene fiber electrode built in accordance with some embodiments of the present disclosure.

FIG. 34 illustrates the placement of a unipolar electrode 3401 around the vagus nerve 3403 and shows the sensitive recording of increase nerve activity evoked by mild hypoxia at 560 uV peak to peak (Panel B of FIG. 34), that is 9-18 fold increased sensitivity compared to that reported with carbon nanotube fibers in the same nerve.

In other configurations the Pt-Gph fiber may be attached to a disposable needle for suture, and use to join tissue portions in patients. Sutures are traditionally made of silk or synthetic materials, and are not conductive.

Figure 35:
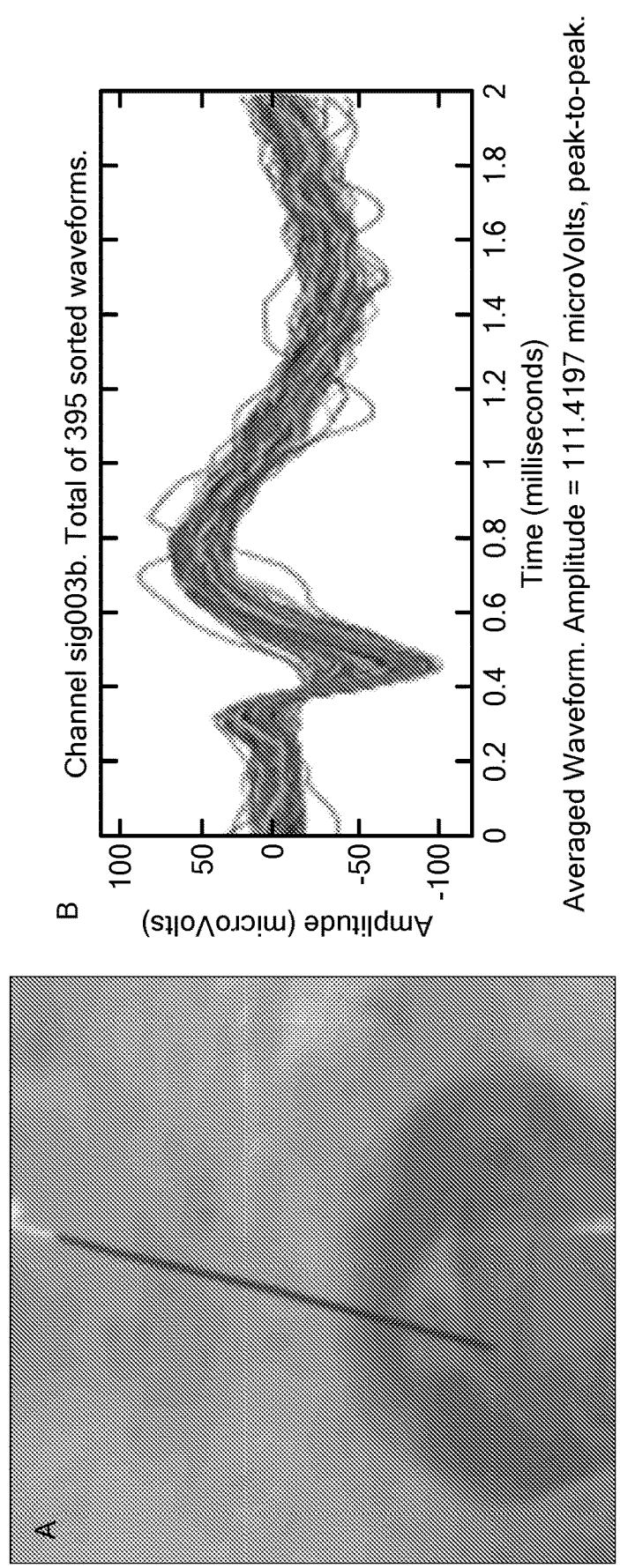
FIG. 35 provides implantation characteristics and neural recordings for a metallized graphene fiber electrode built in accordance with some embodiments of the present disclosure.

As illustrated in FIG. 35, in a separate configuration the GF-Pt fibers can be used as cortical electrodes for recording or stimulation of brain or spinal cord tissue. The GP-Pt fibers can be inserted into the tissue or, in the case of the spinal cord, be tied around the dorsal or ventral roots for sensory and motor interfacing. Stimulation of the dorsal roots can be used to control pain. Panel A illustrated a photograph of an electrode inserted into the rat cerebral cortex. Panel B of FIG. 35 illustrates a single unit recording from a cortical neuron recorded by the GF-Pt electrode.

Figure 36:
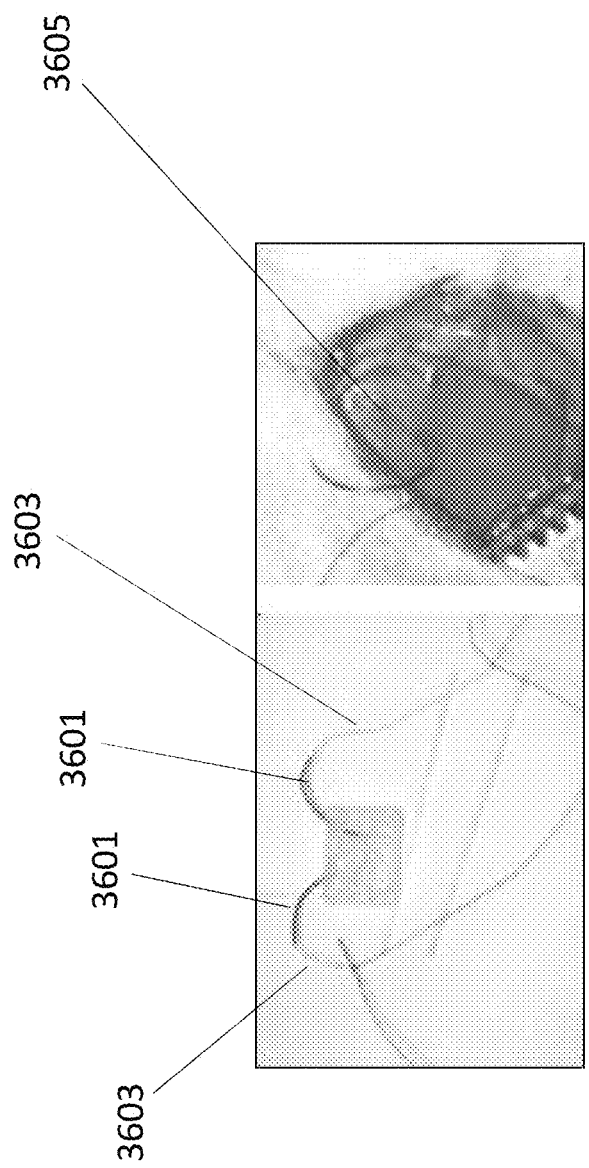
FIG. 36 provides implantation characteristics for a metallized graphene fiber electrode built in accordance with some embodiments of the present disclosure.

As illustrated in FIG. 36, the GF-Pt fibers can be use also to record and stimulate other tissue including skeletal muscle, either epi or intramuscular. Panel A of FIG. 36 illustrates the use of a needle 3601 where the nylon suture 3603 is tied to the GF-Pt. Panel B of FIG. 36 illustrates an embodiment where the GP-Pt fiber is driven into the muscle 3605.

The metallized graphene fibers described herein may be manufactured using. Alternatively, or additionally, metallized graphene fibers may also be produced by 3D printing, extrusion, wet spinning and the like.

The metallized graphene fibers described herein may be used in connection with any suitable muscle. For example, they can be used into the heart as for pace makers or to record arrhythmias, it can also be used over the skin, for transcutaneous of subdermal stimulation. Additional application includes facial muscle muscles for the treatment for ptosis, or migraines. This technology can be also used directly on other organs including the stomach, the liver, the kidney and spleen.

In some configurations, the metallized graphene fibers described herein may be used to cell-culture recordings, biochemical biosensing, molecular bio sensing and the like. For example, unmodified or functionalized graphene fibers can be used to measure extracellular concentration of a number of metabolic and biochemical biomarkers. These include reactive oxygen species such as hydrogen peroxide and oxygen, as well as a number of important neurotransmitters including serotonin, dopamine, glutamate, gamma aminobutyric acid. Metabolic biomarker include glucose, caffeic acid, and estradiol. Further, these can be used as single biosensors or as multi-functional sensor array, and for a broad range of samples including serum, urine, sweat, saliva, and others alike.

In some configurations the fiber electrode may be connected to a battery or to a wireless system for recording or stimulation. In other embodiments, it may be connected to electrical, thermal or radiofrequency energy sources, and be used for electrochemical detection including that of dopamine. They also can be incorporated as a component of other devices, including being part of a nerve scaffold where the sutures that keep the nerve scaffold in place are also conductive and can deliver electrical stimulation to stimulate nerve regeneration. An additional application can be transcutaneous placement of these fibers for applications similar to those in acupuncture, with the advantage that these fibers can be placed once and access as needed. These GP-Pt fibers can be used to treat conditions addressed by acupuncture and others.

In some embodiments, the platinized graphene fibers described herein may be used to record from and stimulate multiple tissues and organs. For example the metallized graphene fibers may be placed onto other organs such as the spleen, kidney, and the like. In some embodiments, electrodes built in accordance with the present disclosure can be wrapped around blood vessels or neuro-vascular plexi for biosensing or neuromodulation. Further, electrodes can be implanted inside, sutured through or over internal organs, including but not limited to, heart, lungs, stomach, liver, spleen, pancreas and other pelvic organs.

For example, in some embodiments the flexibility and sensitivity of the fibers may allow for the placement of these graphene fiber based electrodes on small neurovascular plexi in the spleen, kidney, and other gastric and pelvic organs and ganglia alike. In particular, in the spleen terminal neurovascular branches, the graphene fibers can detect different types of spontaneous and evoked activity in the form of compound action potentials. From these recording and evoking their activity, for example the contribution of specific groups of nerve fiber types to the compound action potentials including A-alpha, A-beta, A-gamma, A-delta/B, and C fibers may be estimated. Further, stimulation of the splenic nerve may be used to neuromodulate the physiological activity of the spleen, including the release of inflammatory cytokines, which may be beneficial as a bioelectronic medical approach for diseases including Rheumatoid Arthritis and Crohn's and the like.

Further, disclosed embodiments may be used for the neuromodulation of somatic and autonomic ganglia, including, for example, the nodose ganglia, carotid ganglia, and the mesenteric and splachnic ganglia and alike. The disclosed fibers may be directly inserted into neurogenic organs with intrinsic neural networks such as the heart or the gut, so as to directly neuromodulate their activity.

The platinized graphene fibers may be used as an implantable conductive suture for neural and neuro-muscular interfaces in chronic applications. For example, the described platinized graphene fibers may be used to record, stimulate, and/or block potentials in nerve and neuromuscular junctions thereby providing a safe and long-term interface with high injection charge capacity, adaptability for a variety of muscles and nerve geometries including those blood vessels-nerve plexus complexes, and high electrode sensitivity.

Embodiments built in accordance with the present disclosure may be used to stimulate a number of tissues in the body including nerves and muscles for the prevention of muscle atrophy age-related, in rehabilitation to recover movements in limbs in paraplegic patients and in those treatments that require punctual electrical stimulation, such as tibial nerve stimulation and pelvic floor for the treatment of urinary incontinence and stimulation of muscles in the knee for osteoarthritis. Further, embodiments built in accordance with the present disclosure may also be used as bidirectional link with robotic prosthetic devices, peripheral neuromodulation and bioelectronic medicine applications.

For example, a method of neural stimulation and/or neural recording may include the step of implanting an electrode built in accordance with the disclosure herein, in-vivo on nerves that control internal organs including brain, heart, spleen, liver, kidneys and the like.

In another example, a method of neural stimulation and/or neural recording may include the step of implanting an electrode built in accordance with the disclosure herein, in-vivo directly on organs including brain, heart muscles both superficially or into the organs.

In yet another example, a method of implantation may include the step of placing an electrode built in accordance with the disclosure herein over tissue, inside the tissue or sutured through or over the tissue.

Optionally, electrodes built in accordance with the disclosure herein may be used to stimulate a set of electrically responsive cells including neurons and muscles cells by sending a current through one or multiple implantable electrode. Additionally, activity from electrogenic cells including neurons and muscle cells by via the implantable electrodes built in accordance with the disclosures herein.

As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined above to provide additional guidance to the practitioner regarding the description of the compositions and methods.

All patents, patent applications, and other scientific or technical writings referred to anywhere herein are incorporated by reference herein in their entirety. The embodiments illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

Although the present disclosure has been described in relation to particular embodiments thereof, many other variations and modifications and other uses will become apparent to those skilled in the art. It is preferred, therefore, that the present disclosure be limited not by the specific disclosure herein, but only by the appended claims.

What is claimed is:

1. An implantable electrode comprising:
a multi-layer graphene-fiber core;
an insulative coating surrounding the multi-layer graphene-fiber core; and
a metal layer disposed between the multi-layer graphene-fiber core and the insulative coating.

2. The implantable electrode of claim 1, wherein the multi-layer graphene-fiber core does not include a binder material.

3. The implantable electrode of claim 1, wherein the insulative coating is a polymer-based coating.

4. The implantable electrode of claim 3, wherein the insulative coating is Parylene-C.

5. The implantable electrode of claim 3, wherein the insulative coating has a thickness between about 1 to 3 μm.

6. The implantable electrode of claim 1, wherein the metal layer is adjacent the multi-layer graphene-fiber core and the metal layer covers a surface portion of the graphene-fiber core with partial encapsulation of the multi-layer graphene-fiber core.

7. The implantable electrode of claim 6, wherein the metal layer covers about half of the surface of the multi-layer graphene-fiber core.

8. The implantable electrode of claim 1, wherein the metal layer is adjacent the multi-layer graphene-fiber core and the metal layer covers a surface portion of the graphene-fiber core with complete encapsulation of the multi-layer graphene-fiber core.

9. The implantable electrode of claim 1, wherein the metal layer comprises at least one of platinum, iridium, iridium oxide, platinum-iridium, and titanium nitride.

10. The implantable electrode of claim 1, wherein the metal layer has thickness in the range between about 10 nm to about 500 nm.

11. The implantable electrode of claim 1, wherein the multi-layer graphene-fiber core has a diameter in the range of between about 10 μm to about 200 μm.

12. A method for making an implantable electrode comprising:
forming a multi-layered graphene-fiber core by performing an in-situ reduction of fully ordered graphene oxide sheets in a liquid crystalline;
coating at least a portion of the multi-layered graphene-fiber core with a metal layer; and
coating the multi-layered graphene-fiber core and metal layer with an insulative coating.

13. The method of claim 12, wherein forming the multi-layered graphene-fiber core by performing the in-situ reduction further comprises a step of wet-spinning liquid crystalline dispersions of graphene oxide using a coagulation bath containing an acid.

14. The method of claim 13 wherein the acid is hypophosphorous acid.

15. The method of claim 12, wherein the metal layer comprises at least one of platinum, iridium, iridium oxide, platinum-iridium, and titanium nitride.

16. The method of claim 12, wherein the metal layer has thickness in the range between about 10 nm to about 500 nm.

17. The method of claim 12, wherein the insulative coating comprises Parylene-C.

18. A method of recording and stimulating a peripheral nerve comprising:
exposing and isolating a target nerve from a surrounding tissue;
engaging an implantable electrode to the target nerve by at least one of passing the implantable electrode about the exposed target nerve and forming a knot with the implantable electrode, and inserting the implantable electrode through an epineurium of the exposed target nerve, wherein the implantable electrode further comprises a multi-layer graphene-fiber core, an insulative coating surrounding the multi-layer graphene fiber core, and a metal layer disposed between the multi-layer graphene-fiber core and the insulative coating; and
at least one of recording and stimulating from the peripheral nerve.

19. The method of claim 18, wherein engaging the peripheral nerve comprises implanting the implantable electrode inside the peripheral nerve, sutured through the peripheral nerve, or over the peripheral nerve.

20. The method of claim 18, wherein the peripheral nerve is peripheral to at least one of a heart, lungs, stomach, liver, spleen, pancreas and pelvic organs.

* * * * *